US006596536B1

(12) United States Patent
Hercend et al.

(10) Patent No.: US 6,596,536 B1
(45) Date of Patent: Jul. 22, 2003

(54) NUCLEOTIDE SEQUENCES CODING FOR VARIABLE REGIONS OF THE ALPHA CHAINS OF HUMAN T LYMPHOCYTE RECEPTORS, CORRESPONDING PEPTIDE SEGMENTS AND THE DIAGNOSTIC AND THERAPEUTIC USES

(75) Inventors: Thierry Hercend, Nogent-sur Marne (FR); Frederic Triebel, Seine (FR); Sergio Roman-Roman, Paris (FR); Laurent Ferradini, Paris (FR)

(73) Assignee: Aventis Pharma S.A. (FR)

( * ) Notice: Subject to any disclaimer, the term of this patent is extended or adjusted under 35 U.S.C. 154(b) by 0 days.

(21) Appl. No.: 08/442,001

(22) Filed: May 16, 1995

Related U.S. Application Data

(62) Division of application No. 08/348,572, filed on Dec. 2, 1994, now Pat. No. 5,817,511, which is a continuation of application No. 07/934,529, filed as application No. PCT/FR92/00111 on Feb. 7, 1992, now abandoned.

(30) Foreign Application Priority Data

Feb. 8, 1991 (FR) .............................................. 91 01487
Apr. 12, 1991 (FR) .............................................. 91 04527

(51) Int. Cl.$^7$ ....................... C07K 16/28; C07K 19/00; C12N 5/20; A61K 39/395
(52) U.S. Cl. ................ 435/343.2; 424/133.1; 424/143.1; 424/144.1; 424/154.1; 424/173.1; 424/178.1; 424/183.1; 424/809; 435/326; 435/334; 435/346; 530/387.1; 530/388.22; 530/388.75; 530/389.6; 530/391.1; 530/391.3; 530/391.7; 530/808; 530/866

(58) Field of Search ................... 424/133.1, 143.1, 424/144.1, 154.1, 173.1, 178.1, 183.1, 809; 435/326, 334, 343.2, 346; 530/387.1, 388.22, 388.75, 389.6, 391.1, 391.3, 391.7, 808, 866; 935/89, 104, 107

(56) References Cited

U.S. PATENT DOCUMENTS 5,223,426 A * 6/1993 Skibbens et al. ........... 435/331

OTHER PUBLICATIONS

Goding, "Monoclonal Antibodies: Principles and Practice", Academic Press, pp. 29–31, 48–58, 1986.*
Wilson et al., Imm. Rev., 101: 149–172.*
Waldmann, Science, 252: 1657–1662, 1991.*
Harris et al., TIBTECH, 11: 42–44, 1993.*

* cited by examiner

*Primary Examiner*—Ronald B. Schwadron
(74) *Attorney, Agent, or Firm*—Muserlian, Lucas and Mercanti

(57) ABSTRACT

An isolated antibody that specifically binds a peptide coded by a nucleotide sequence coding for a variable region of α chain of an human T lymphocyte receptor, said nucleotide sequence having a nucleotide sequence chosen from any of:

Vα segments having any one of the sequences SEQ ID Nos. 1 to 11 or

Jα segments having one of the sequence SEQ ID Nos. 13 or 15 to 19 and hybridomas producing said antibodies.

6 Claims, 5 Drawing Sheets

Vα1

```
                        1
IGRa08      AGTGTTCCCTTGCTCAGCCATGCTCCTGGAGCTTATCCCACTGCTGGGGATACATTTTGTCCTGAGAACTGCCAGAGCCCAGTCAGTGACCAGCCTGA
IGRa08      CATCCACATCACTGTCTCTGAAGGAGCCTCACTGGAGTTGAGATGTAACTATTCCTATGGGCAACACACCTTATCTCTTCTGGTATGTCCAGTCCCCGGC
IGRa08      CAAGGCCTCCAGCTCCTGAAGTACTTTTCAGGAGACACTCTGGTTCAAGGCATTAAAGGCTTTGAGGCTGAATTAAGAGGAGTCAATCTTCCTTCA
IGRa08/AE11
IGRa08      ACCTGAGGAAACCCTCTGTGCATTGGAGTGATGCTGCTGAGTACTTCTGTGCT    333
IGRa08/AE11                                         .T        102
```

```
IGRa09                                                   AAATCCTTGAGAGTTTTACTAGTGATCCTGTGGCTTCAGCTGAGCCGGGTTTGGAGCCAACAGAAGGAGGTGGAGCA
IGRa09      GAATTCTGGACCCCTCAGTGTTCCAGAGGGAGCCATTGCCTCTCTCAACTGCACTTACAGTGACCGAGGTTCCCAGTCCTTCTTCTGGTACAGACAATAT
IGRa09/AF110
IGRa09      TCTGGGAAAAGCCCTGAGTTGATAATGTCCATATACTCCAATGGTGACAAAGAAGATGGAAGGTTTACAGCACAGCTCAATAAAGCCAGCCAGTATGTTT
IGRa09/AF110  .
IGRa09      CTCTGCTCATCAGAGACTCCCAGCCCAGTGATTCAGCCACCTACCTCTGTGCC    330
IGRa09/AF110                                                     252
```

```
IGRα10      GGCCACATTTGGGGAGACGAAATGGAGTCATCCCTGGGAGGTGTTTTGCTGATTTTGTGGCTTCAAGTGGACTGGGTGAAGAGCCAAAAGATAGAACAGAA
                                1
IGRα10      TTCCGAGGCCCTGAACATTCAGGAGGGTAAAACGGCCACCCTGACCTGCAACTATACAAACTATTCTCCAGCATACTTACAGTGGTACCGACAAGATCCA
HAP35       ................................................................................................

IGRα10      GGAAGAGGCCCTGTTTTCTTGCTACTCATACGTGAAAATGAGAAATGAGAAAAGGAAAGAAGACTGAAGGTCACCTTTGATACCACCCTTAAACAGAGTT
HAP35       ................................................................................................

IGRα10      TGTTTCATATCACAGCCTCCCAGCCTGCAGACTCAGCTACCTACCTCTGTGCT       333
HAP35       ..................................................       249
```

```
IGRα11      CTCGTGGTATCCTGCAGCAGAATGTGGGGAGTTTCCTTCTTTATGTTTCCATGAAGATGGGAGGCACTACAGGACAAAACATTGACCAGCCCACTGAGAT
                                 1
IGRα11      GACAGCTACGGAAGGTGCCATTGTCCAGATCAACTGCACGTACCAGACATCTGGGTTCAACGGGCTGTTCTGGTACCAGCAACATGCTGGGCGAAGCACCC
HAP12       ................................................................................................

IGRα11      ACATTTCTGTCTTCTTACAATGTTCTGGATGGTTTGGAGGAGAAAAGGTCGTTTTTCTTCATTCCTTAGTCGGTCGTTACCTCCTTTTGAAGG
HAP12       ................................................................................................

IGRα11      AGCTCCAGATGAAAGACTCTGCCTCTTACCTCTGTGCT       318
HAP12       .....................................       222
```

FIG. 1D

```
Vα22       
IGRa12     ATTTGGGTAACACACTAAAGATGAACTATTCTCCAGGCTTAGTATCTCTGATACTCTTACTGCTTGGAGAAGAACCGTGGAGATTCAGTGACCCAGATGGA

IGRa12     AGGGCCAGTGACTCTCTCAGAAGAGAGCCCTTCCTGACTATAAACTGCACGTACACAGGATACCCTTCCCTTTTCTGGTATGTCCAATATCCTGGA

IGRa12     GAAGGTCTACAGCTCCTCCTGAAAGCCACGAAGGCTGATGACAAGGGAAGCAACAAAGGTTTTGAAGCCACATACGTAAAGAAACCACTTCTTTCCACT
AC9

IGRa12     TGGAGAAAGGCTCAGTTCAAGTGTCAGACTTCAGCGGTGTACTTCTGTGCT    330
AC9                                                           113
```

FIG. 1E

```
                                                              F  G  G  T
IGRJa01G   GGTTATTGCAATAGCACTAAAGACTGTGTAACACCAATGCAGGCAAATCAACCTTGGGGATCCCGGACTACGCTCACTGTGAAGCCA
IGRJa02G   GGTTTGTAAAAGAATGAGCCATTGTGGATAGGCTTTGCTGCATTGCGGGTCCCGGCACTCAAGTGATTGTTTTACCA
IGRJa04                                                    TAGATACTGGAGGCTTCAAAACTATCTTCAAAACGTCTTCTTTGGAGCAGGAACAAGAACTATTTGTTAAAGCA
IGRJa05                                                    CCTAACTGGGGCAAGGCCAAGGAAATCTCATCTTGGGACTGGAAGACTCACCGTTCTCTCC
IGRJa06                                                    ATGGAGGAAGCCAAGGAAATCTCATCTTGGAAGAGGCACTAAACTCTCTGTTAAACCA
IGRJa07                                                            GGAGCTGGCTACAATAAGCTAAGCTGACATTTTGAAAAGGAAGCAGGAGACCAGGCTGAGTGTTAGACCA
IGRJa08                                                            CTGGTGGCTACAATAAGCTAAGCTGATTTCTTTGGAAGCTCAGGGACCAGGCTGGCTGTACACCCA
IGRJa09                                                               TGGAAACAAGCTGGTCTTTGGCGCAGGAACCATTCTGAGAGTCAAGTCC
```

FIG. 2

SEQUENCE LISTING

<160> NUMBER OF SEQ ID NOS: 84

<210> SEQ ID NO 1
<211> LENGTH: 371
<212> TYPE: DNA
<213> ORGANISM: Homo sapiens
<220> FEATURE:
<221> NAME/KEY: misc_feature
<223> OTHER INFORMATION: Clone IGR a 02, T Cell Receptor V Alpha w24
      gene segment, CDS nucleotides 36-371 (for amino acid sequence,
      see SEQ ID NO:66)

<400> SEQUENCE: 1
agtcaacttc tgggagcagt ctctgcagaa taaaaatgaa aaagcatctg acgaccttct      60
tggtgatttt gtggctttat ttttataggg ggaatggcaa aaaccaagtg gagcagagtc     120
ctcagtccct gatcatcctg gagggaaaga actgcactct tcaatgcaat tatacagtga     180
gccccttcag caacttaagg tggtataagc aagatactgg gagaggtcct gtttccctga     240
caatcatgac tttcagtgag aacacaaagt cgaacggaag atatacagca actctggatg     300
cagacacaaa gcaaagctct ctgcacatca cagcctccca gctcagcgat tcagcctcct     360
acatctgtgt g                                                          371

<210> SEQ ID NO 2
<211> LENGTH: 400
<212> TYPE: DNA
<213> ORGANISM: HOMO SAPIENS
<220> FEATURE:
<221> NAME/KEY: misc_feature
<223> OTHER INFORMATION: Clone IGR a 03, T Cell Receptor V Alpha w25
      gene segment, CDS nucleotides 77-400 (for amino acid sequence,
      see SEQ ID NO:67)

<400> SEQUENCE: 2
gactctaagc ccaagagagt ttcttgaagc aaaaaaaaaa aaaacccatt caggaaataa      60
ttctttgctg ataaggatgc tccttgaaca tttattaata atcttgtgga tgcagctgac     120
atgggtcagt ggtcaacagc tgaatcagag tcctcaatct atgtttatcc aggaaggaga     180
agatgtctcc atgaactgca cttcttcaag catatttaac acctggctat ggtacaagca     240

```
ggaccctggg gaaggtcctg tcctcttgat agccttatat aaggctggtg aattgacctc      300
aaatggaaga ctgactgctc agtttggtat aaccagaaag gacagcttcc tgaatatctc      360
agcatccata cctagtgatg taggcatcta cttctgtgct                            400
```

<210> SEQ ID NO 3
<211> LENGTH: 339
<212> TYPE: DNA
<213> ORGANISM: HOMO SAPIENS
<220> FEATURE:
<221> NAME/KEY: misc_feature
<223> OTHER INFORMATION: Clone IGR a 04, T Cell Receptor V Alpha w26
      gene segment, CDS nucleotides 10-339 (for amino acid sequence,
      see SEQ ID NO:68)

<400> SEQUENCE: 3

```
agctaaggga tggagactgt tctgcaagta ctcctaggga tattggggtt ccaagcagcc      60
tgggtcagta gccaagaact ggagcagagt cctcagtcct tgatcgtcca agagggaaag     120
aatctcacca taaactgcac gtcatcaaag acgttatatg cttatactg gtataagcaa     180 aagtatggtg aaggtcttat cttcttgatg atgctacaga aggtggggga agagaaaagt     240
catgaaaaga taactgccaa gttggatgag aaaaagcagc aaagttccct gcatatcaca     300
gcctcccagc ccagccatgc aggcatctac tctgtggga                            339
```

<210> SEQ ID NO 4
<211> LENGTH: 335
<212> TYPE: DNA
<213> ORGANISM: HOMO SAPIENS
<220> FEATURE:
<221> NAME/KEY: misc_feature
<223> OTHER INFORMATION: Clone IGR a 05, T Cell Receptor V Alpha w27
      gene segment, CDS nucleotides 78-335 (for amino acid sequence,
      see SEQ ID NO:69)

<400> SEQUENCE: 4

```
agaaaaaaaa aatgaagaag ctactagcaa tgatcctgtg gcttcaacta gaccggttaa      60
gtggagagct gaaagtggaa caaaaccctc tgttcctgag catgcaggag ggaaaaaact     120
ataccatcta ctgcaattat tcaaccactt cagacagact gtattggtac aggcaggatc     180
ctgggaaaag tctggaatct ctgtttgtgt tgctatcaaa tggagcagtg aagcaggagg     240
gacgattaat ggcctcactt gataccaaag cccgtctcag caccctccac atcacagctg     300
ccgtgcatga cctctctgcc acctacttct gtgcc                                335
```

<210> SEQ ID NO 5
<211> LENGTH: 361
<212> TYPE: DNA
<213> ORGANISM: HOMO SAPIENS
<220> FEATURE:
<221> NAME/KEY: misc_feature
<223> OTHER INFORMATION: Clone IGR a 07, T Cell Receptor V Alpha w29
      gene segment, CDS nucleotides 32-361 (for amino acid sequence,
      see SEQ ID NO:70)

<400> SEQUENCE: 5

```
gaagctgact ggatattctg gcaggccaag gatggagact ctcctgaaag tgccttcagg      60
caccttgttg tggcagttga cctgggtggg aagccaacaa ccagtgcaga gtcctcaagc     120
cgtgatcctc cgagaagggg aagatgctgt caccaactgc agttcctcca aggctttata     180
ttctgtacac tggtacaggc agaagcatgg tgaagcaccc gtcttcctga tgatattact     240
gaagggtgga gaacagatgc gtcgtgaaaa aatatctgct tcatttaatg aaaaaaagca     300
```

```
gcaaagctcc ctgtacctta cggcctccca gctcagttac tcaggaacct acttctgcgg    360
g                                                                    361
```

```
<210> SEQ ID NO 6
<211> LENGTH: 569
<212> TYPE: DNA
<213> ORGANISM: HOMO SAPIENS
<220> FEATURE:
<221> NAME/KEY: misc_feature
<223> OTHER INFORMATION: Clone IGR a 08, T Cell Receptor V Alpha 1 gene
      segment, CDS nucleotides 237-569 (for amino acid sequence,
      see SEQ ID NO:71)

<400> SEQUENCE: 6
tcagtttctt cttcctgcag ctggttgagt tctttccaga caaagacaag tgacaagaat     60
tagaggttta aaaagcaacc agattcatct cagcagcttt tgtagtttta aataagcaag    120
gagtttctcc agcgaaactt cctcacacct cttggtcttg gtctcttcag acactttcct    180
tcctgttctc tggagatctt gcagaaaaga gcctgcagtg tttcccttgc tcagccatgc    240
tcctggagct tatcccactg ctggggatac attttgtcct gagaactgcc agagcccagt    300
cagtgaccca gcctgacatc cacatcactg tctctgaagg agcctcactg gagttgagat    360
gtaactattc ctatgggca acaccttatc tcttctggta tgtccagtcc cccggccaag    420
gcctccagct gctcctgaag tacttttcag gagacactct ggttcaaggc attaaaggct    480
ttgaggctga atttaagagg agtcaatctt ccttcaacct gaggaaaccc tctgtgcatt    540
ggagtgatgc tgctgagtac ttctgtgct                                      569
```

```
<210> SEQ ID NO 7
<211> LENGTH: 330
<212> TYPE: DNA
<213> ORGANISM: HOMO SAPIENS
<220> FEATURE:
<221> NAME/KEY: misc_feature
<223> OTHER INFORMATION: Clone IGR a 09, T Cell Receptor V Alpha 2 gene
      segment, CDS 1-330 (for amino acid sequence, see SEQ ID NO:72)

<400> SEQUENCE: 7
aaatccttga gagttttact agtgatcctg tggcttcagc tgagccgggt ttggagccaa     60
cagaaggagg tggagcagaa ttctggaccc tcagtgttc cagagggagc cattgcctct    120
ctcaactgca cttacagtga ccgaggttcc cagtccttct tctggtacag acaatattct    180
gggaaaagcc ctgagttgat aatgtccata tactccaatg gtgacaaaga agatggaagg    240
tttacagcac agctcaataa agccagccag tatgtttctc tgctcatcag agactcccag    300
cccagtgatt cagccaccta cctctgtgcc                                     330
```

```
<210> SEQ ID NO 8
<211> LENGTH: 400
<212> TYPE: DNA
<213> ORGANISM: HOMO SAPIENS
<220> FEATURE:
<221> NAME/KEY: misc_feature
<223> OTHER INFORMATION: Clone IGR a10, T Cell Receptor V Alpha 5 gene
      segment, CDS nucleotides 68-400 (for amino acid sequence,
      see SEQ ID NO:73)

<400> SEQUENCE: 8
gccaaacaga atggcttttt ggctgagaag gctgggtcta catttcaggc cacatttggg     60
gagacgaatg gagtcatccc tgggaggtgt tttgctgatt ttgtggcttc aagtggactg    120
```

```
ggtgaagagc caaaagatag aacagaattc cgaggccctg aacattcagg agggtaaaac      180
ggccaccctg acctgcaact atacaaacta ttctccagca tacttacagt ggtaccgaca      240
agatccagga agaggccctg ttttcttgct actcatacgt gaaaatgaga aagaaaaaag      300
gaaagaaaga ctgaaggtca cctttgatac cacccttaaa cagagtttgt ttcatatcac      360
agcctcccag cctgcagact cagctaccta cctctgtgct                            400
```

<210> SEQ ID NO 9
<211> LENGTH: 386
<212> TYPE: DNA
<213> ORGANISM: HOMO SAPIENS
<220> FEATURE:
<221> NAME/KEY: misc_feature
<223> OTHER INFORMATION: Clone IGR a11, T Cell Receptor V Alpha 7 gene
      segment, CDS nucleotides 69-386 (for amino acid sequence,
      see SEQ ID NO:74)

<400> SEQUENCE: 9

```
gccttctgca gactccaatg gctcaggaac tgggaatgca gtgccaggct cgtggtatcc      60
tgcagcagat gtggggagtt ttccttcttt atgtttccat gaagatggga ggcactacag     120
gacaaaacat tgaccagccc actgagatga cagctacgga aggtgccatt gtccagatca     180
actgcacgta ccagacatct gggttcaacg ggctgttctg gtaccagcaa catgctggcg     240
aagcacccac atttctgtct tacaatgttc tggatggttt ggaggagaaa ggtcgttttt     300
cttcattcct tagtcggtct aaagggtaca gttacctcct tttgaaggag ctccagatga     360
aagactctgc ctcttacctc tgtgct                                          386
```

<210> SEQ ID NO 10
<211> LENGTH: 383
<212> TYPE: DNA
<213> ORGANISM: HOMO SAPIENS
<220> FEATURE:
<221> NAME/KEY: misc_feature
<223> OTHER INFORMATION: Clone IGR a12, T Cell Receptor V Alpha 22 gene
      segment, CDS nucleotides 64-383 (for amino acid sequence
      see SEQ ID NO:75)

<400> SEQUENCE: 10

```
tgtgacttct tcatgttaag gatcaagacc attatttggg taacacacta aagatgaact      60
attctccagg cttagtatct ctgatactct tactgcttgg aagaacccgt ggagattcag     120
tgacccagat ggaagggcca gtgactctct cagaagaggc cttcctgact ataaactgca     180
cgtacacagc cacaggatac ccttcccttt tctggtatgt ccaatatcct ggagaaggtc     240
tacagctcct cctgaaagcc acgaaggctg atgacaaggc aagcaacaaa ggttttgaag     300
ccacataccg taaagaaacc acttctttcc acttggagaa aggctcagtt caagtgtcag     360
actcagcggt gtacttctgt gct                                             383
```

<210> SEQ ID NO 11
<211> LENGTH: 364
<212> TYPE: DNA
<213> ORGANISM: HOMO SAPIENS
<220> FEATURE:
<221> NAME/KEY: misc_feature
<223> OTHER INFORMATION: Clone IGR a13, T Cell Receptor V Alpha 16 gene
      segment, CDS nucleotides 32-364 (for amino acid sequence,
      see SEQ ID NO:76)

<400> SEQUENCE: 11

```
aatcccgccc gccgtgagct tagctggagc catggcctct gcacccatct cgatgcttgc      60
```

-continued

```
gatgctcttc acattgagtg ggctgagagc tcagtcagtg gctcagccgg aagatcaggt      120
caacgttgct gaagggaatc tctgactgt  gaaatgcacc tattcagtct ctggaaaccc      180 ttatctttt  tggtatgttc aatacccca  ccgaggcctc cagttccttc tgaaatacat      240 cacagggat  aacctggtta aaggcagcta tggctttgaa gctgaattta acaagagcca      300
aacctccttc cacctgaaga aaccatctgc cttgtgagc  gactccgctt tgtacttctg      360
tgct                                                                   364
```

<210> SEQ ID NO 12
<211> LENGTH: 263
<212> TYPE: DNA
<213> ORGANISM: HOMO SAPIENS
<220> FEATURE:
<221> NAME/KEY: misc_feature
<223> OTHER INFORMATION: Clone Ja 01, T Cell Receptor J Alpha gene
      segment, CDS nucleotides 207-263 (for amino acid sequence,
      see SEQ ID NO:77)

<400> SEQUENCE: 12

```
ccttcaagga aaattaaggc aaatagaatt gggctgggga gttgctactt attagtattc       60
ctcccacgtt ctaacctaat tataaggagg ttgttttggc catgggcagt catctcaggt      120
tttgttttcc tgctttcctc cctaacctcc acctgtcttc ctagaggcct gagtcaaggt      180
tattgcaata gcactaaaga ctgtgtaaca ccaatgcagg caaatcaacc tttggggatg      240
ggactacgct cactgtgaag cca                                              263
```

<210> SEQ ID NO 13
<211> LENGTH: 277
<212> TYPE: DNA
<213> ORGANISM: HOMO SAPIENS
<220> FEATURE:
<221> NAME/KEY: misc_feature
<223> OTHER INFORMATION: Clone Ja 02, T Cell Receptor J Alpha gene
      segment,CDS 221-277 (for amino acid sequence, see SEQ ID NO:78)

<400> SEQUENCE: 13

```
aaggacacag actgcctgca tgaaggctgg agctgggccc aggatgagga aaggcctcag       60
gaaggaaggg ctgacacgaa ataaggaata ccatggcatt catgagatgt gcgtctgaat      120
cctctctctt gcctgagaag ctttagcttc caccttgaga cacaaaacat gtggttatga      180
agagatgaca aggttttttgt aaaagaatga gccattgtgg ataggctttg ggaatgtgct     240
gcattgcggg tccggcactc aagtgattgt tttacca                                277
```

<210> SEQ ID NO 14
<211> LENGTH: 60
<212> TYPE: DNA
<213> ORGANISM: HOMO SAPIENS
<220> FEATURE:
<221> NAME/KEY: misc_feature
<223> OTHER INFORMATION: Clone Ja 05, T Cell Receptor J Alpha gene
      segment, CDS 3-59 (for amino acid sequence, see SEQ ID NO:79)

<400> SEQUENCE: 14

```
tagatactgg aggcttcaaa actatctttg gagcaggaac aagactattt gttaaagcaa       60
```

<210> SEQ ID NO 15
<211> LENGTH: 59
<212> TYPE: DNA
<213> ORGANISM: HOMO SAPIENS
<220> FEATURE:
<221> NAME/KEY: misc_feature

```
<223> OTHER INFORMATION: Clone Ja 05, T Cell Receptor J Alpha gene
      segment, CDS nucleotides 2-58 (for amino acid sequence,
      see SEQ ID NO:80)

<400> SEQUENCE: 15
cctaactggg gcaaacaacg tcttctttgg gactggaacg agactcaccg ttcttccct        59

<210> SEQ ID NO 16
<211> LENGTH: 60
<212> TYPE: DNA
<213> ORGANISM: HOMO SAPIENS
<220> FEATURE:
<221> NAME/KEY: misc_feature
<223> OTHER INFORMATION: Clone Ja 06, T Cell Receptor J Alpha gene
      segment, CDS nucleotides 3-59 (for amino acid sequence,
      see SEQ ID NO:81)

<400> SEQUENCE: 16
atggaggaag ccaaggaaat ctcatctttg gaaaaggcac taaactctct gttaaaccaa       60

<210> SEQ ID NO 17
<211> LENGTH: 56
<212> TYPE: DNA
<213> ORGANISM: HOMO SAPIENS
<220> FEATURE:
<221> NAME/KEY: misc_feature
<223> OTHER INFORMATION: Clone Ja 07, T Cell Receptor J Alpha gene
      segment, CDS 1-54 (for amino acid sequence, see SEQ ID NO:82)

<400> SEQUENCE: 17
ggagccaata gtaagctgac atttggaaaa ggataactc tgagtgttag accaga           56

<210> SEQ ID NO 18
<211> LENGTH: 57
<212> TYPE: DNA
<213> ORGANISM: HOMO SAPIENS
<220> FEATURE:
<221> NAME/KEY: misc_feature
<223> OTHER INFORMATION: Clone Ja 08, T Cell Receptor J Alpha gene
      segment, CDS nucleotides 3-56 (for amino acid sequence,
      see SEQ ID NO:83)

<400> SEQUENCE: 18
ctggtggcta caataagctg attttttggag cagggaccag gctggctgta cacccat         57

<210> SEQ ID NO 19
<211> LENGTH: 50
<212> TYPE: DNA
<213> ORGANISM: HOMO SAPIENS
<220> FEATURE:
<221> NAME/KEY: misc_feature
<223> OTHER INFORMATION: Clone Ja 09, T Cell Receptor J Alpha gene
      segment, CDS nucleotides 2-49 (for amino acid sequence,
      see SEQ ID NO:84)

<400> SEQUENCE: 19
tggaaacaag ctggtctttg gcgcaggaac cattctgaga gtcaagtcct                  50

<210> SEQ ID NO 20
<211> LENGTH: 22
<212> TYPE: DNA
<213> ORGANISM: OLIGONUCLEOTIDE

<400> SEQUENCE: 20
gttgctccag gccacagcac tg                                                22

<210> SEQ ID NO 21
```

```
<211> LENGTH: 35
<212> TYPE: DNA
<213> ORGANISM: OLIGONUCLEOTIDE

<400> SEQUENCE: 21
gcatgcgcgc ggccgcggag gccccccccc ccccc                              35

<210> SEQ ID NO 22
<211> LENGTH: 26
<212> TYPE: DNA
<213> ORGANISM: OLIGONUCLEOTIDE

<400> SEQUENCE: 22
gtccatagac ctcatgtcca gcacag                                        26

<210> SEQ ID NO 23
<211> LENGTH: 24
<212> TYPE: DNA
<213> ORGANISM: OLIGONUCLEOTIDE

<400> SEQUENCE: 23
atacacatca gaattcttac tttg                                          24

<210> SEQ ID NO 24
<211> LENGTH: 19
<212> TYPE: DNA
<213> ORGANISM: OLIGONUCLEOTIDE

<400> SEQUENCE: 24
gtcactggat ttagagtct                                                19

<210> SEQ ID NO 25
<211> LENGTH: 24
<212> TYPE: DNA
<213> ORGANISM: OLIGONUCLEOTIDE
<220> FEATURE:
<221> NAME/KEY: misc_feature
<223> OTHER INFORMATION: OLIGONUCLEOTIDE, Type V Alpha 1, Clone AB22,
      Position 235, the 6th and 23rd nucleotides correspond
      to mismatches introduced relative to the natural sequence

<400> SEQUENCE: 25
ggcattaacg gttttgaggc tgga                                          24

<210> SEQ ID NO 26
<211> LENGTH: 24
<212> TYPE: DNA
<213> ORGANISM: OLIGONUCLEOTIDE
<220> FEATURE:
<221> NAME/KEY: misc_feature
<223> OTHER INFORMATION: OLIGONUCLEOTIDE, Type V Alpha 2, Clone IGRa09,
      Position 93*, the 24th nucleotide corresponds to a mismatch
      introduced relative to the natural sequence.

<400> SEQUENCE: 26
cagtgttcca gagggagcca ttgc                                          24

<210> SEQ ID NO 27
<211> LENGTH: 24
<212> TYPE: DNA
<213> ORGANISM: OLIGONUCLEOTIDE
<220> FEATURE:
<221> NAME/KEY: misc_feature
<223> OTHER INFORMATION: OLIGONUCLEOTIDE, Type V Alpha 3, Clone HAP05,
      Position 297

<400> SEQUENCE: 27
```
ccgggcagca gacactgctt ctta                                          24

<210> SEQ ID NO 28
<211> LENGTH: 24
<212> TYPE: DNA
<213> ORGANISM: OLIGONUCLEOTIDE
<220> FEATURE:
<221> NAME/KEY: misc_feature
<223> OTHER INFORMATION: OLIGONUCLEOTIDE, Type V Alpha 4, Clone HAP08,
      Position 153

<400> SEQUENCE: 28
ttggtatcga cagcttccct ccca                                          24

<210> SEQ ID NO 29
<211> LENGTH: 24
<212> TYPE: DNA
<213> ORGANISM: OLIGONUCLEOTIDE
<220> FEATURE:
<221> NAME/KEY: misc_feature
<223> OTHER INFORMATION: OLIGONUCLEOTIDE, Type V Alpha 5, Clone IGRa10,
      Position 113

<400> SEQUENCE: 29
cggccaccct gacctgcaac tata                                          24

<210> SEQ ID NO 30
<211> LENGTH: 24
<212> TYPE: DNA
<213> ORGANISM: OLIGONUCLEOTIDE
<220> FEATURE:
<221> NAME/KEY: misc_feature
<223> OTHER INFORMATION: OLIGONUCLEOTIDE, TYPE V Alpha 6, CLONE HAP01,
      POSITION 287

<400> SEQUENCE: 30
tccgccaacc ttgtcatctc cgct                                          24

<210> SEQ ID NO 31
<211> LENGTH: 24
<212> TYPE: DNA
<213> ORGANISM: OLIGONUCLEOTIDE
<220> FEATURE:
<221> NAME/KEY: misc_feature
<223> OTHER INFORMATION: OLIGONUCLEOTIDE, TYPE V Alpha 7, CLONE IGRa11,
      POSITION 159, THE 9TH AND 15TH NUCLEOTIDES CORRESPOND TO
      MISMATCHES INTRODUCED RELATIVE TO THE NATURAL SEQUENCE

<400> SEQUENCE: 31
gcaacatgct ggcggagcac ccac                                          24

<210> SEQ ID NO 32
<211> LENGTH: 24
<212> TYPE: DNA
<213> ORGANISM: OLIGONUCLEOTIDE
<220> FEATURE:
<221> NAME/KEY: misc_feature
<223> OTHER INFORMATION: OLIGONUCLEOTIDE, TYPE V Alpha 8, CLONE HAP41,
      POSITION 204

<400> SEQUENCE: 32
cattcgttca aatgtgggca aaag                                          24

<210> SEQ ID NO 33
<211> LENGTH: 24
<212> TYPE: DNA
<213> ORGANISM: OLIGONUCLEOTIDE

```
<220> FEATURE:
<221> NAME/KEY: misc_feature
<223> OTHER INFORMATION: OLIGONUCLEOTIDE, TYPE V Alpha 9, CLONE HAVP36,
      POSITION 168, THE 22ND NUCLEOTIDE CORRESPONDS TO A MISMATCH
      INTRODUCED RELATIVE TO THE NATURAL SEQUENCE

<400> SEQUENCE: 33
ccagtactcc agacaacgcc tgca                                              24

<210> SEQ ID NO 34
<211> LENGTH: 24
<212> TYPE: DNA
<213> ORGANISM: OLIGONUCLEOTIDE
<220> FEATURE:
<221> NAME/KEY: misc_feature
<223> OTHER INFORMATION: OLIGONUCLEOTIDE, TYPE V Alpha 10, CLONE HAP58,
      POSITION 282

<400> SEQUENCE: 34
cactgcggcc cagcctggtg atac                                              24

<210> SEQ ID NO 35
<211> LENGTH: 24
<212> TYPE: DNA
<213> ORGANISM: OLIGONUCLEOTIDE
<220> FEATURE:
<221> NAME/KEY: misc_feature
<223> OTHER INFORMATION: OLIGONUCLEOTIDE, TYPE V Alpha 11, CLONE AB19,
      POSITION 254*

<400> SEQUENCE: 35
cgctgctcat cctccaggtg cggg                                              24

<210> SEQ ID NO 36
<211> LENGTH: 24
<212> TYPE: DNA
<213> ORGANISM: OLIGONUCLEOTIDE
<220> FEATURE:
<221> NAME/KEY: misc_feature
<223> OTHER INFORMATION: OLIGONUCLEOTIDE, TYPE V Alpha 12, CLONE
      V12MA483, POSITION 213

<400> SEQUENCE: 36
tcgtcggaac tcttttgatg agca                                              24

<210> SEQ ID NO 37
<211> LENGTH: 24
<212> TYPE: DNA
<213> ORGANISM: OLIGONUCLEOTIDE
<220> FEATURE:
<221> NAME/KEY: misc_feature
<223> OTHER INFORMATION: OLIGONUCLEOTIDE, TYPE V Alpha 13, CLONE HAVT15,
      POSITION 152*

<400> SEQUENCE: 37
ttcatcaaaa cccttgggga cagc                                              24

<210> SEQ ID NO 38
<211> LENGTH: 24
<212> TYPE: DNA
<213> ORGANISM: OLIGONUCLEOTIDE
<220> FEATURE:
<221> NAME/KEY: misc_feature
<223> OTHER INFORMATION: OLIGONUCLEOTIDE, TYPE V Alpha 14, CLONE HAVT20,
      POSITION 181

<400> SEQUENCE: 38
cccagcaggc agatgattct cgtt                                              24
```

<210> SEQ ID NO 39
<211> LENGTH: 24
<212> TYPE: DNA
<213> ORGANISM: OLIGONUCLEOTIDE
<220> FEATURE:
<221> NAME/KEY: misc_feature
<223> OTHER INFORMATION: OLIGONUCLEOTIDE, TYPE V Alpha 15, CLONE HAVT31,
      POSITION 278, THE 12TH NUCLEOTIDE CORRESPONDS TO A MISMATCH
      INTRODUCED RELATIVE TO THE NATURAL SEQUENCE

<400> SEQUENCE: 39
ttgcagacac cgagactggg gact                                          24

<210> SEQ ID NO 40
<211> LENGTH: 24
<212> TYPE: DNA
<213> ORGANISM: OLIGONUCLEOTIDE
<220> FEATURE:
<221> NAME/KEY: misc_feature
<223> OTHER INFORMATION: OLIGONUCLEOTIDE, TYPE V Alpha 16, CLONE IGRa13,
      POSITION 89

<400> SEQUENCE: 40
tcaacgttgc tgaagggaat cctc                                          24

<210> SEQ ID NO 41
<211> LENGTH: 24
<212> TYPE: DNA
<213> ORGANISM: OLIGONUCLEOTIDE
<220> FEATURE:
<221> NAME/KEY: misc_feature
<223> OTHER INFORMATION: OLIGONUCLEOTIDE, TYPE V Alpha 17, CLONE AB11,
      POSITION 204, THE 12TH NUCLEOTIDE CORRESPONDS TO A MISMATCH
      INTRODUCED RELATIVE TO THE NATURAL SEQUENCE

<400> SEQUENCE: 41
tgggaaaggc cgtgcattat tgat                                          24

<210> SEQ ID NO 42
<211> LENGTH: 24
<212> TYPE: DNA
<213> ORGANISM: OLIGONUCLEOTIDE
<220> FEATURE:
<221> NAME/KEY: misc_feature
<223> OTHER INFORMATION: OLIGONUCLEOTIDE, TYPE V Alpha 18, CLONE AB21,
      POSITION 114

<400> SEQUENCE: 42
cagcaccaat ttcacctgca gctt                                          24

<210> SEQ ID NO 43
<211> LENGTH: 24
<212> TYPE: DNA
<213> ORGANISM: OLIGONUCLEOTIDE
<220> FEATURE:
<221> NAME/KEY: misc_feature
<223> OTHER INFORMATION: OLIGONUCLEOTIDE, TYPE V Alpha 19, CLONE AC24,
      POSITION 162

<400> SEQUENCE: 43
acactggctg caacagcatc cagg                                          24

<210> SEQ ID NO 44
<211> LENGTH: 24
<212> TYPE: DNA
<213> ORGANISM: OLIGONUCLEOTIDE
<220> FEATURE:

```
<221> NAME/KEY: misc_feature
<223> OTHER INFORMATION: OLIGONUCLEOTIDE, TYPE V Alpha 20, CLONE AE212,
      POSITION 232

<400> SEQUENCE: 44
tccctgttta tccctgccga caga                                              24

<210> SEQ ID NO 45
<211> LENGTH: 24
<212> TYPE: DNA
<213> ORGANISM: OLIGONUCLEOTIDE
<220> FEATURE:
<221> NAME/KEY: misc_feature
<223> OTHER INFORMATION: OLIGONUCLEOTIDE, TYPE V Alpha 21, CLONE AF211,
      POSITION 92

<400> SEQUENCE: 45
agcaaaattc accatccctg agcg                                              24

<210> SEQ ID NO 46
<211> LENGTH: 24
<212> TYPE: DNA
<213> ORGANISM: OLIGONUCLEOTIDE
<220> FEATURE:
<221> NAME/KEY: misc_feature
<223> OTHER INFORMATION: OLIGONUCLEOTIDE, TYPE V Alpha 22, CLONE IGRa12,
      POSITION 197

<400> SEQUENCE: 46
cctgaaagcc acgaaggctg atga                                              24

<210> SEQ ID NO 47
<211> LENGTH: 24
<212> TYPE: DNA
<213> ORGANISM: OLIGONUCLEOTIDE
<220> FEATURE:
<221> NAME/KEY: misc_feature
<223> OTHER INFORMATION: OLIGONUCLEOTIDE, TYPE V Alpha w23, CLONE
      IGRa01, POSITION 246

<400> SEQUENCE: 47
tgcctcgctg gataaatcat cagg                                              24

<210> SEQ ID NO 48
<211> LENGTH: 24
<212> TYPE: DNA
<213> ORGANISM: OLIGONUCLEOTIDE
<220> FEATURE:
<221> NAME/KEY: misc_feature
<223> OTHER INFORMATION: OLIGONUCLEOTIDE, TYPE V Alpha w24, CLONE
      IGRa02,POSITION 259, THE 21ST NUCLEOTIDE CORRESPONDS TO A
      MISMATCH INTRODUCED RELATIVE TO THE NATURAL SEQUENCE

<400> SEQUENCE: 48
ctggatgcag acacaaagca gagc                                              24

<210> SEQ ID NO 49
<211> LENGTH: 24
<212> TYPE: DNA
<213> ORGANISM: OLIGONUCLEOTIDE
<220> FEATURE:
<221> NAME/KEY: misc_feature
<223> OTHER INFORMATION: OLIGONUCLEOTIDE, TYPE V Alpha w25, CLONE
      IGRA03, POSITION 148, THE 7TH AND 17TH NUCLEOTIDES CORRESPOND TO
      MISMATCHES INTRODUCED RELATIVE TO THE NATURAL SEQUENCE

<400> SEQUENCE: 49
tggctacggt acaagccgga ccct                                              24
```

<210> SEQ ID NO 50
<211> LENGTH: 24
<212> TYPE: DNA
<213> ORGANISM: OLIGONUCLEOTIDE
<220> FEATURE:
<221> NAME/KEY: misc_feature
<223> OTHER INFORMATION: OLIGONUCLEOTIDE, TYPE V Alpha w26, CLONE
      IGRa04, POSITION 299, THE 4TH AND 20TH NUCLEOTIDES CORRESPOND TO
      MISMATCHES INTRODUCED RELATIVE TO THE NATURAL SEQUENCE

<400> SEQUENCE: 50
agcgcagcca tgcaggcatg tacc                                             24

<210> SEQ ID NO 51
<211> LENGTH: 24
<212> TYPE: DNA
<213> ORGANISM: OLIGONUCLEOTIDE
<220> FEATURE:
<221> NAME/KEY: misc_feature
<223> OTHER INFORMATION: OLIGONUCLEOTIDE, TYPE V Alpha w27, CLONE
      IGRa05, POSITION 268*

<400> SEQUENCE: 51
aagcccgtct cagcaccctc caca                                             24

<210> SEQ ID NO 52
<211> LENGTH: 24
<212> TYPE: DNA
<213> ORGANISM: OLIGONUCLEOTIDE
<220> FEATURE:
<221> NAME/KEY: misc_feature
<223> OTHER INFORMATION: OLIGONUCLEOTIDE, TYPE V Alpha w28, CLONE
      IGRa06, POSITION 95, THE 8TH AND 15TH NUCLEOTIDES CORRESPOND TO
      MISMATCHES INTRODUCED RELATIVE TO THE NATURAL SEQUENCE

<400> SEQUENCE: 52
tggttgtgca cgagcgagac actg                                             24

<210> SEQ ID NO 53
<211> LENGTH: 24
<212> TYPE: DNA
<213> ORGANISM: OLIGONUCLEOTIDE
<220> FEATURE:
<221> NAME/KEY: misc_feature
<223> OTHER INFORMATION: OLIGONUCLEOTIDE, TYPE V Alpha w29, CLONE
      IGRa07, POSITION 210

<400> SEQUENCE: 53
gaagggtgga gaacagatgc gtcg                                             24

<210> SEQ ID NO 54
<211> LENGTH: 24
<212> TYPE: DNA
<213> ORGANISM: OLIGONUCLEOTIDE
<220> FEATURE:
<221> NAME/KEY: misc_feature
<223> OTHER INFORMATION: OLIGONUCLEOTIDE, TYPE C Alpha A, POSITION 129

<400> SEQUENCE: 54
atacacatca gaattcttac tttg                                             24

<210> SEQ ID NO 55
<211> LENGTH: 24
<212> TYPE: DNA
<213> ORGANISM: OLIGONUCLEOTIDE
<220> FEATURE:
<221> NAME/KEY: misc_feature
<223> OTHER INFORMATION: OLIGONUCLEOTIDE, TYPE C Alpha B, POSITION 201

<400> SEQUENCE: 55
gttgctccag ccgcggcac tgtt                              24

<210> SEQ ID NO 56
<211> LENGTH: 19
<212> TYPE: DNA
<213> ORGANISM: OLIGONUCLEOTIDE
<220> FEATURE:
<221> NAME/KEY: misc_feature
<223> OTHER INFORMATION: OLIGONUCLEOTIDE, TYPE C Alpha C, POSITION 57

<400> SEQUENCE: 56
gtcactggat ttagagtct                                   19

<210> SEQ ID NO 57
<211> LENGTH: 24
<212> TYPE: DNA
<213> ORGANISM: OLIGONUCLEOTIDE
<220> FEATURE:
<221> NAME/KEY: misc_feature
<223> OTHER INFORMATION: OLIGONUCLEOTIDE, TYPE Act 1, CLONE Beta-actin,
      POSITION 1161

<400> SEQUENCE: 57
atttgcggtg gacgatggag gggc                             24

<210> SEQ ID NO 58
<211> LENGTH: 24
<212> TYPE: DNA
<213> ORGANISM: OLIGONUCLEOTIDE
<220> FEATURE:
<221> NAME/KEY: misc_feature
<223> OTHER INFORMATION: OLIGONUCLEOTIDE, TYPE Act 2, CLONE Beta-ACTIN,
      POSITION 261

<400> SEQUENCE: 58
ggcatcgtca ccaactggga cgac                             24

<210> SEQ ID NO 59
<211> LENGTH: 19
<212> TYPE: DNA
<213> ORGANISM: OLIGONUCLEOTIDE
<220> FEATURE:
<221> NAME/KEY: misc_feature
<223> OTHER INFORMATION: OLIGONUCLEOTIDE, TYPE Act 3, CLONE Beta-ACTIN,
      POSITION 642

<400> SEQUENCE: 59
accaccacgg cggagcggg                                   19

<210> SEQ ID NO 60
<211> LENGTH: 24
<212> TYPE: DNA
<213> ORGANISM: OLIGONUCLEOTIDE
<220> FEATURE:
<221> NAME/KEY: misc_feature
<223> OTHER INFORMATION: OLIGONUCLEOTIDE, TYPE C Beta F, POSITION 135

<400> SEQUENCE: 60
cgggctgctc cttgaggggc tgcg                             24

<210> SEQ ID NO 61
<211> LENGTH: 19
<212> TYPE: DNA
<213> ORGANISM: OLIGONUCLEOTIDE

```
<220> FEATURE:
<221> NAME/KEY: misc_feature
<223> OTHER INFORMATION: OLIGONUCLEOTIDE, TYPE C Beta K, POSITION 20

<400> SEQUENCE: 61
cccacccgag gtcgctgtg                                              19

<210> SEQ ID NO 62
<211> LENGTH: 19
<212> TYPE: DNA
<213> ORGANISM: OLIGONUCLEOTIDE
<220> FEATURE:
<221> NAME/KEY: misc_feature
<223> OTHER INFORMATION: OLIGONUCLEOTIDE, TYPE C Beta C, POSITION 58

<400> SEQUENCE: 62
tctgcttctg atggctcaa                                              19

<210> SEQ ID NO 63
<211> LENGTH: 102
<212> TYPE: DNA
<213> ORGANISM: HOMO SAPIENS
<220> FEATURE:
<221> NAME/KEY: misc_feature
<223> OTHER INFORMATION: AE11

<400> SEQUENCE: 63
ggcattaaag gctttgaggc tgaatttaag aggagtcaat cttccttcaa tctgaggaaa    60
ccctctgtgc attggagtga tgctgctgag tacttctgtg ct                     102

<210> SEQ ID NO 64
<211> LENGTH: 7
<212> TYPE: PRT
<213> ORGANISM: PEPTIDE
<220> FEATURE:
<221> NAME/KEY: MISC_FEATURE
<223> OTHER INFORMATION: KLEIN ET AL., PROC. NATL. ACAD. SCI. USA, VOL.
      84,
      PAGE 6884, 1987.

<400> SEQUENCE: 64

His Ser Thr Cys Ala Tyr Met
1               5

<210> SEQ ID NO 65
<211> LENGTH: 5
<212> TYPE: PRT
<213> ORGANISM: PEPTIDE
<220> FEATURE:
<221> NAME/KEY: MISC_FEATURE
<222> LOCATION: (3)..(3)
<223> OTHER INFORMATION: CONSERVED AMINO ACID SEQUENCE IN J ALPHA
      SEGMENTS, X AT POSITION 3 MAY BE ANY AMINO ACID.

<400> SEQUENCE: 65

Phe Gly Xaa Gly Thr
1               5

<210> SEQ ID NO 66
<211> LENGTH: 112
<212> TYPE: PRT
<213> ORGANISM: HOMO SAPIENS
<220> FEATURE:
<221> NAME/KEY: MISC_FEATURE
<223> OTHER INFORMATION: TRANSLATION OF NUCLEOTIDES 36-371 OF SEQ ID
      NO:1

<400> SEQUENCE: 66
```

Met Lys Lys His Leu Thr Thr Phe Leu Val Ile Leu Trp Leu Tyr Phe
1               5                   10                  15

Tyr Arg Gly Asn Gly Lys Asn Gln Val Glu Gln Ser Pro Gln Ser Leu
            20                  25                  30

Ile Ile Leu Glu Gly Lys Asn Cys Thr Leu Gln Cys Asn Tyr Thr Val
            35                  40                  45

Ser Pro Phe Ser Asn Leu Arg Trp Tyr Lys Gln Asp Thr Gly Arg Gly
50                  55                  60

Pro Val Ser Leu Thr Ile Met Thr Phe Ser Glu Asn Thr Lys Ser Asn
65                  70                  75                  80

Gly Arg Tyr Thr Ala Thr Leu Asp Ala Asp Thr Lys Gln Ser Ser Leu
                85                  90                  95

His Ile Thr Ala Ser Gln Leu Ser Asp Ser Ala Ser Tyr Ile Cys Val
            100                 105                 110

<210> SEQ ID NO 67
<211> LENGTH: 108
<212> TYPE: PRT
<213> ORGANISM: HOMO SAPIENS
<220> FEATURE:
<221> NAME/KEY: MISC_FEATURE
<223> OTHER INFORMATION: TRANSLATION OF NUCLEOTIDES 77-400 OF SEQ ID
      NO:2

<400> SEQUENCE: 67

Met Leu Leu Glu His Leu Leu Ile Ile Leu Trp Met Gln Leu Thr Trp
1               5                   10                  15

Val Ser Gly Gln Gln Leu Asn Gln Ser Pro Gln Ser Met Phe Ile Gln
            20                  25                  30

Glu Gly Glu Asp Val Ser Met Asn Cys Thr Ser Ser Ser Ile Phe Asn
            35                  40                  45

Thr Trp Leu Trp Tyr Lys Gln Asp Pro Gly Glu Gly Pro Val Leu Leu
50                  55                  60

Ile Ala Leu Tyr Lys Ala Gly Glu Leu Thr Ser Asn Gly Arg Leu Thr
65                  70                  75                  80

Ala Gln Phe Gly Ile Thr Arg Lys Asp Ser Phe Leu Asn Ile Ser Ala
                85                  90                  95

Ser Ile Pro Ser Asp Val Gly Ile Tyr Phe Cys Ala
            100                 105

<210> SEQ ID NO 68
<211> LENGTH: 110
<212> TYPE: PRT
<213> ORGANISM: HOMO SAPIENS
<220> FEATURE:
<221> NAME/KEY: MISC_FEATURE
<223> OTHER INFORMATION: TRANSLATION OF NUCLEOTIDES 10-339 OF SEQ ID
      NO:3

<400> SEQUENCE: 68

Met Glu Thr Val Leu Gln Val Leu Leu Gly Ile Leu Gly Phe Gln Ala
1               5                   10                  15

Ala Trp Val Ser Ser Gln Gln Leu Glu Gln Ser Pro Gln Ser Leu Ile
            20                  25                  30

Val Gln Glu Gly Lys Asn Leu Thr Ile Asn Cys Thr Ser Ser Lys Thr
            35                  40                  45

Leu Tyr Gly Leu Tyr Trp Tyr Lys Gln Lys Tyr Gly Glu Gly Leu Ile
50                  55                  60

```
Phe Leu Met Met Leu Gln Lys Gly Gly Glu Lys Ser His Glu Lys
 65                  70                  75                  80

Ile Thr Ala Lys Leu Asp Glu Lys Lys Gln Gln Ser Ser Leu His Ile
                 85                  90                  95

Thr Ala Ser Gln Pro Ser His Ala Gly Ile Tyr Leu Cys Gly
            100                 105                 110
```

<210> SEQ ID NO 69
<211> LENGTH: 86
<212> TYPE: PRT
<213> ORGANISM: HOMO SAPIENS
<220> FEATURE:
<221> NAME/KEY: MISC_FEATURE
<223> OTHER INFORMATION: TRANSLATION OF NUCLEOTIDES 78-335 OF SEQ ID
      NO:4

<400> SEQUENCE: 69

```
Glu Gln Asn Pro Leu Phe Leu Ser Met Gln Glu Gly Lys Asn Tyr Thr
 1               5                  10                  15

Ile Tyr Cys Asn Tyr Ser Thr Thr Ser Asp Arg Leu Tyr Trp Tyr Arg
                20                  25                  30

Gln Asp Pro Gly Lys Ser Leu Glu Ser Leu Phe Val Leu Leu Ser Asn
            35                  40                  45

Gly Ala Val Lys Gln Glu Gly Arg Leu Met Ala Ser Leu Asp Thr Lys
        50                  55                  60

Ala Arg Leu Ser Thr Leu His Ile Thr Ala Ala Val His Asp Leu Ser
 65                  70                  75                  80

Ala Thr Tyr Phe Cys Ala
                85
```

<210> SEQ ID NO 70
<211> LENGTH: 110
<212> TYPE: PRT
<213> ORGANISM: HOMO SAPIENS
<220> FEATURE:
<221> NAME/KEY: MISC_FEATURE
<223> OTHER INFORMATION: TRANSLATION OF NUCLEOTIDES 32-361 OF SEQ ID
      NO:5

<400> SEQUENCE: 70

```
Met Glu Thr Leu Leu Lys Val Pro Ser Gly Thr Leu Leu Trp Gln Leu
 1               5                  10                  15

Thr Trp Val Gly Ser Gln Gln Pro Val Gln Ser Pro Gln Ala Val Ile
                20                  25                  30

Leu Arg Glu Gly Glu Asp Ala Val Thr Asn Cys Ser Ser Ser Lys Ala
            35                  40                  45

Leu Tyr Ser Val His Trp Tyr Arg Gln Lys His Gly Glu Ala Pro Val
        50                  55                  60

Phe Leu Met Ile Leu Leu Lys Gly Gly Glu Gln Met Arg Arg Glu Lys
 65                  70                  75                  80

Ile Ser Ala Ser Phe Asn Glu Lys Lys Gln Gln Ser Ser Leu Tyr Leu
                85                  90                  95

Thr Ala Ser Gln Leu Ser Tyr Ser Gly Thr Tyr Phe Cys Gly
            100                 105                 110
```

<210> SEQ ID NO 71
<211> LENGTH: 111
<212> TYPE: PRT
<213> ORGANISM: HOMO SAPIENS
<220> FEATURE:
<221> NAME/KEY: MISC_FEATURE

<223> OTHER INFORMATION: TRANSLATION OF NUCLEOTIDES 237-569 OF SEQ ID
     NO:6

<400> SEQUENCE: 71

Met Leu Leu Glu Leu Ile Pro Leu Leu Gly Ile His Phe Val Leu Arg
1               5                   10                  15

Thr Ala Arg Ala Gln Ser Val Thr Gln Pro Asp Ile His Ile Thr Val
            20                  25                  30

Ser Glu Gly Ala Ser Leu Glu Leu Arg Cys Asn Tyr Ser Tyr Gly Ala
        35                  40                  45

Thr Pro Tyr Leu Phe Trp Tyr Val Gln Ser Pro Gly Gln Gly Leu Gln
    50                  55                  60

Leu Leu Leu Lys Tyr Phe Ser Gly Asp Thr Leu Val Gln Gly Ile Lys
65                  70                  75                  80

Gly Phe Glu Ala Glu Phe Lys Arg Ser Gln Ser Ser Phe Asn Leu Arg
                85                  90                  95

Lys Pro Ser Val His Trp Ser Asp Ala Ala Glu Tyr Phe Cys Ala
            100                 105                 110

<210> SEQ ID NO 72
<211> LENGTH: 110
<212> TYPE: PRT
<213> ORGANISM: HOMO SAPIENS
<220> FEATURE:
<221> NAME/KEY: MISC_FEATURE
<223> OTHER INFORMATION: TRANSLATION OF NUCLEOTIDES 1-330 OF SEQ ID
     NO:7

<400> SEQUENCE: 72

Lys Ser Leu Arg Val Leu Val Ile Leu Trp Leu Gln Leu Ser Arg
1               5                   10                  15

Val Trp Ser Gln Gln Lys Glu Val Glu Gln Asn Ser Gly Pro Leu Ser
            20                  25                  30

Val Pro Glu Gly Ala Ile Ala Ser Leu Asn Cys Thr Tyr Ser Asp Arg
        35                  40                  45

Gly Ser Gln Ser Phe Phe Trp Tyr Arg Gln Tyr Ser Gly Lys Ser Pro
    50                  55                  60

Glu Leu Ile Met Ser Ile Tyr Ser Asn Gly Asp Lys Glu Asp Gly Arg
65                  70                  75                  80

Phe Thr Ala Gln Leu Asn Lys Ala Ser Gln Tyr Val Ser Leu Leu Ile
                85                  90                  95

Arg Asp Ser Gln Pro Ser Asp Ser Ala Thr Tyr Leu Cys Ala
            100                 105                 110

<210> SEQ ID NO 73
<211> LENGTH: 111
<212> TYPE: PRT
<213> ORGANISM: HOMO SAPIENS
<220> FEATURE:
<221> NAME/KEY: MISC_FEATURE
<223> OTHER INFORMATION: TRANSLATION OF NUCLEOTIDES 68-400 OF SEQ ID
     NO:8

<400> SEQUENCE: 73

Met Glu Ser Ser Leu Gly Gly Val Leu Leu Ile Leu Trp Leu Gln Val
1               5                   10                  15

Asp Trp Val Lys Ser Gln Lys Ile Glu Gln Asn Ser Glu Ala Leu Asn
            20                  25                  30

Ile Gln Glu Gly Lys Thr Ala Thr Leu Thr Cys Asn Tyr Thr Asn Tyr
        35                  40                  45

```
Ser Pro Ala Tyr Leu Gln Trp Tyr Arg Gln Asp Pro Gly Arg Gly Pro
        50                  55                  60

Val Phe Leu Leu Leu Ile Arg Glu Asn Glu Lys Glu Lys Arg Lys Glu
 65                  70                  75                  80

Arg Leu Lys Val Thr Phe Asp Thr Thr Leu Lys Gln Ser Leu Phe His
                 85                  90                  95

Ile Thr Ala Ser Gln Pro Ala Asp Ser Ala Thr Tyr Leu Cys Ala
                100                 105                 110

<210> SEQ ID NO 74
<211> LENGTH: 106
<212> TYPE: PRT
<213> ORGANISM: HOMO SAPIENS
<220> FEATURE:
<221> NAME/KEY: MISC_FEATURE
<223> OTHER INFORMATION: TRANSLATION OF NUCLEOTIDES 69-386 OF SEQ ID
      NO:9

<400> SEQUENCE: 74

Met Trp Gly Val Phe Leu Leu Tyr Val Ser Met Lys Met Gly Gly Thr
 1               5                  10                  15

Thr Gly Gln Asn Ile Asp Gln Pro Thr Glu Met Thr Ala Thr Glu Gly
                20                  25                  30

Ala Ile Val Gln Ile Asn Cys Thr Tyr Gln Thr Ser Gly Phe Asn Gly
                35                  40                  45

Leu Phe Trp Tyr Gln Gln His Ala Gly Glu Ala Pro Thr Phe Leu Ser
        50                  55                  60

Tyr Asn Val Leu Asp Gly Leu Glu Glu Lys Gly Arg Phe Ser Ser Phe
 65                  70                  75                  80

Leu Ser Arg Ser Lys Gly Tyr Ser Tyr Leu Leu Leu Lys Glu Leu Gln
                 85                  90                  95

Met Lys Asp Ser Ala Ser Tyr Leu Cys Ala
                100                 105

<210> SEQ ID NO 75
<211> LENGTH: 110
<212> TYPE: PRT
<213> ORGANISM: HOMO SAPIENS
<220> FEATURE:
<221> NAME/KEY: MISC_FEATURE
<223> OTHER INFORMATION: TRANSLATION OF NUCLEOTIDES 64-383 OF SEQ ID
      NO:10

<400> SEQUENCE: 75

Met Asn Tyr Ser Pro Gly Leu Val Ser Leu Ile Leu Leu Leu Leu Gly
 1               5                  10                  15

Arg Thr Arg Gly Asp Ser Val Thr Gln Met Glu Gly Pro Val Thr Leu
                20                  25                  30

Ser Glu Glu Ala Phe Leu Thr Ile Asn Cys Thr Tyr Thr Ala Thr Gly
                35                  40                  45

Tyr Pro Ser Leu Phe Trp Tyr Val Gln Tyr Pro Gly Glu Gly Leu Gln
        50                  55                  60

Leu Leu Leu Lys Ala Thr Lys Ala Asp Asp Lys Gly Ser Asn Lys Gly
 65                  70                  75                  80

Phe Glu Ala Thr Tyr Arg Lys Glu Thr Thr Ser Phe His Leu Glu Lys
                 85                  90                  95

Gly Ser Val Gln Val Ser Asp Ser Ala Val Tyr Phe Cys Ala
                100                 105                 110
```

<210> SEQ ID NO 76
<211> LENGTH: 111
<212> TYPE: PRT
<213> ORGANISM: HOMO SAPIENS
<220> FEATURE:
<221> NAME/KEY: MISC_FEATURE
<223> OTHER INFORMATION: TRANSLATION OF NUCLEOTIDES 32-364 OF SEQ ID
      NO:11

<400> SEQUENCE: 76

Met Ala Ser Ala Pro Ile Ser Met Leu Ala Met Leu Phe Thr Leu Ser
1               5                   10                  15

Gly Leu Arg Ala Gln Ser Val Ala Gln Pro Glu Asp Gln Val Asn Val
            20                  25                  30

Ala Glu Gly Asn Pro Leu Thr Val Lys Cys Thr Tyr Ser Val Ser Gly
        35                  40                  45

Asn Pro Tyr Leu Phe Trp Tyr Val Gln Tyr Pro Asn Arg Gly Leu Gln
    50                  55                  60

Phe Leu Leu Lys Tyr Ile Thr Gly Asp Asn Leu Val Lys Gly Ser Tyr
65                  70                  75                  80

Gly Phe Glu Ala Glu Phe Asn Lys Ser Gln Thr Ser Phe His Leu Lys
                85                  90                  95

Lys Pro Ser Ala Leu Val Ser Asp Ser Ala Leu Tyr Phe Cys Ala
            100                 105                 110

<210> SEQ ID NO 77
<211> LENGTH: 19
<212> TYPE: PRT
<213> ORGANISM: HOMO SAPIENS
<220> FEATURE:
<221> NAME/KEY: MISC_FEATURE
<223> OTHER INFORMATION: TRANSLATION OF NUCLEOTIDES 207-263 OF SEQ ID
      NO:12

<400> SEQUENCE: 77

Asn Thr Asn Ala Gly Lys Ser Thr Phe Gly Asp Gly Thr Thr Leu Thr
1               5                   10                  15

Val Lys Pro

<210> SEQ ID NO 78
<211> LENGTH: 19
<212> TYPE: PRT
<213> ORGANISM: HOMO SAPIENS
<220> FEATURE:
<221> NAME/KEY: MISC_FEATURE
<223> OTHER INFORMATION: TRANSLATION OF NUCLEOTIDES 221-277 OF SEQ ID
      NO:13

<400> SEQUENCE: 78

Ile Gly Phe Gly Asn Val Leu His Cys Gly Ser Gly Thr Gln Val Ile
1               5                   10                  15

Val Leu Pro

<210> SEQ ID NO 79
<211> LENGTH: 19
<212> TYPE: PRT
<213> ORGANISM: HOMO SAPIENS
<220> FEATURE:
<221> NAME/KEY: MISC_FEATURE
<223> OTHER INFORMATION: TRANSLATION OF NUCLEOTIDES 3-59 OF SEQ ID
      NO:14

<400> SEQUENCE: 79

Asp Thr Gly Gly Phe Lys Thr Ile Phe Gly Ala Gly Thr Arg Leu Phe
1               5                   10                  15

Val Lys Ala

<210> SEQ ID NO 80
<211> LENGTH: 19
<212> TYPE: PRT
<213> ORGANISM: HOMO SAPIENS
<220> FEATURE:
<221> NAME/KEY: MISC_FEATURE
<223> OTHER INFORMATION: TRANSLATION OF NUCLEOTIDES 2-58 OF SEQ ID
      NO:15

<400> SEQUENCE: 80

Leu Thr Gly Ala Asn Asn Val Phe Phe Gly Thr Gly Thr Arg Leu Thr
1               5                   10                  15

Val Leu Pro

<210> SEQ ID NO 81
<211> LENGTH: 19
<212> TYPE: PRT
<213> ORGANISM: HOMO SAPIENS
<220> FEATURE:
<221> NAME/KEY: MISC_FEATURE
<223> OTHER INFORMATION: TRANSLATION OF NUCLEOTIDES 3-59 OF SEQ ID
      NO:16

<400> SEQUENCE: 81

Gly Gly Ser Gln Gly Asn Leu Ile Phe Gly Lys Gly Thr Lys Leu Ser
1               5                   10                  15

Val Lys Pro

<210> SEQ ID NO 82
<211> LENGTH: 18
<212> TYPE: PRT
<213> ORGANISM: HOMO SAPIENS
<220> FEATURE:
<221> NAME/KEY: MISC_FEATURE
<223> OTHER INFORMATION: TRANSLATION OF NUCLEOTIDES 1-54 OF SEQ ID
      NO:17

<400> SEQUENCE: 82

Gly Ala Asn Ser Lys Leu Thr Phe Gly Lys Gly Ile Thr Leu Ser Val
1               5                   10                  15

Arg Pro

<210> SEQ ID NO 83
<211> LENGTH: 18
<212> TYPE: PRT
<213> ORGANISM: HOMO SAPIENS
<220> FEATURE:
<221> NAME/KEY: MISC_FEATURE
<223> OTHER INFORMATION: TRANSLATION OF NUCLEOTIDES 3-57 OF SEQ ID
      NO:18

<400> SEQUENCE: 83

Gly Gly Tyr Asn Lys Leu Ile Phe Gly Ala Gly Thr Arg Leu Ala Val
1               5                   10                  15

His Pro

<210> SEQ ID NO 84
<211> LENGTH: 16
<212> TYPE: PRT
<213> ORGANISM: HOMO SAPIENS

-continued

```
<220> FEATURE:
<221> NAME/KEY: MISC_FEATURE
<223> OTHER INFORMATION: TRANSLATION OF NUCLEOTIDES 2-49 OF SEQ ID
      NO:19

<400> SEQUENCE: 84

Gly Asn Lys Leu Val Phe Gly Ala Gly Thr Ile Leu Arg Val Lys Ser
1               5                   10                  15
```

NUCLEOTIDE SEQUENCES CODING FOR VARIABLE REGIONS OF THE ALPHA CHAINS OF HUMAN T LYMPHOCYTE RECEPTORS, CORRESPONDING PEPTIDE SEGMENTS AND THE DIAGNOSTIC AND THERAPEUTIC USES

PRIOR APPLICATIONS

This application is a division of U.S. patent application Ser. No. 08/348,572 filed on Dec. 2, 1994 now U.S. Pat. No. 5,817,511 which is a continuation of U.S. patent application Ser. No. 07/934,529 filed Nov. 24, 1992, now abandoned which is a 371 of PCT FR92/00111 filed Feb. 7, 1992.

The present invention relates to new nucleptide sequences coding for variable regions of α chain T-cell receptors, corresponding peptide segments and the diagnostic and therapeutic uses.

It is known that the receptors recognizing antigens at the surface of mature T lymphocytes (hereafter designated T-cell receptors) possess a structure having a certain similarity with those of immunoglobulins. Therefore, they contain heterodimeric structures containing α and β glycoprotein chains or γ and δ glycoprotein chains (see Meuer et al. (1), Moingeon et al. (2), Brenner et al. (3), Bank et al. (4)).

The directory of T-cell receptors must be able to address the immense diversity of antigenic determinants. This is obtained by genetic recombination of different discontinuous segments of genes which code for the different structural regions of T-cell receptors. Thus, the genes contain V segments (variable segments), optionally D segments (diversity segments), J segments (junction segments) and C segments (constant segments). During the differentiation of T-cells, specific genes are created by recombination of V, D and J segments for the β and δ loci and V and J segments for the α and γ loci. These specific combinations as well as the pairing of two chains create the combinational diversity. This diversity is highly amplified by two supplementary mechanisms, namely the imprecise recombination of V-D-J or V-J segments and the addition of nucleotides corresponding to the N region (Davis et al. (5)).

A certain number of genetic V segments are already known. These segments have been grouped into subfamilies as a function of the similarity of sequences. By definition, the segments which have more than 75% similarity in the nucleotide sequence have been considered as members of the same subfamily (Crews et al. (6)). The known Vα nongenetic segments have also been classified into 22 subfamilies, 14 of which have only one member (see Concannon et al. (7), Kimura et al. (8), Wilson et al. (9)).

Moreover, about 60 J genetic segments have been described (9).

Furthermore, monoclonal antibodies directed against specific segments of the variable parts of T-cell receptors, in particular the β or δ chains, were recently described in WO 90/06758. These monoclonal antibodies are useful not only as diagnostic tools but also as therapeutic tools, for example, vis-à-vis rheumatoid athritis.

The use of synthetic peptides corresponding to the variable regions of the α or β chains in the treatment of auto-immune diseases is also described (23 and 24).

It is also known that variations exist from one individual to another in the expression of different variable segments of the T-cell receptor in man (27 and 28).

The present inventions aims to enrich the directory of genetic segments coding for the variable regions of the chains of T-cell receptors by providing on the one hand new Vα genetic segments belonging to new subfamilies or belonging to subfamilies of which at least one member is already known, and on the other hand, new Jα genetic segments.

Therefore a subject of the present invention is nucleotide sequences coding for the variable regions of α chains of human T lymphocyte receptors, corresponding to cDNA's containing nucleotide sequences chosen from any one of the following:

a—Vα segments corresponding to one of the sequences SEQ ID No. 1 to 11, and b—Jα segments corresponding to one of the sequences SEQ ID No. 12, 13 and 15 to 20, and the sequences which differ from them by one or more nucleotides.

More particularly a subject of the present invention is:

sequences coding for the variable regions of α chains of human T lymphocyte receptors, corresponding to cDNAs containing nucleotide sequences chosen from any one of the Vα segments corresponding to one of the sequences SEQ ID No. 1 to 10 and the sequences which differ from them by one or more nucleotides, sequences coding for the variable regions of α chains of human T lymphocyte receptors, corresponding to cDNAs containing nucleotide sequences chosen from any one of the Jα segments corresponding to one of the sequences SEQ ID No. 12, 13 and 15 to 20 and the sequences which differ from them by one or more nucleotides.

The expression "and sequences which differ from them by one or more nucleotides", encompasses alleles which differ by up to 8 nucleotides, but more often differ by 1 or 2 nucleotides or which can differ by the deletion or addition of one or two codons.

Also a more particular subject of the invention is: nucleotide sequences coding for the variable regions of α chains of human T lymphocyte receptors, corresponding to cDNAs corresponding to all or part of the nucleotide sequences chosen from any one of the Vα segments corresponding to one of the sequences SEQ ID No. 2 to 5, and the sequences which differ from them by one or two nucleotides, nucleotide sequences coding for the variable regions of the α chains of human T lymphocyte receptors, corresponding to cDNAs corresponding to all or part of the nucleotide sequences chosen from any one of the Vα segments corresponding to one of the sequences 1 to 200 of SEQ ID No. 1
1 to 467 of SEQ ID No. 6
1 to 77 of SEQ ID No. 7
1 to 151 of SEQ ID No. 8
291 to 386 of SEQ ID No. 9
1 to 260 of SEQ ID No. 10 and the sequences which differ from them by one or two nucleotides, nucleotide sequences coding for the variable regions of the α chains of human T lymphocyte receptors, corresponding to cDNAs corresponding to all or part of the nucleotide sequence corresponding to SEQ ID No. 11 and which contain the 108 nucleotide, nucleotide sequences coding for the variable regions of the α chains of human T lymphocyte receptors, corresponding to cDNAs corresponding to all or part of the nucleotide sequences chosen from any one of the Jα segments corresponding to one of the sequences SEQ ID No. 12, 13 and 15 to 20 and the sequences which differ from them by one or two nucleotides.

By the expression "nucleotide sequences corresponding to cDNAs corresponding to all or part of the nucleotide sequences" is also designated the complete sequences as well as fragments of these sequences including short fragments (oligonucleotides) which can be used as probes (generally containing at least 10 nucleotides) or as primers (generally containing at least 15 nucleotides). In a general fashion, the invention encompasses the group of new oligonucleotides which are fragments of Vα and Jα sequences according to the invention.

As to the sequences which differ by one or two nucleotides, they correspond to variations which are observed experimentally at the time of determination of the nucleotide sequence of several cDNAs.

Also a subject of the present invention is the peptides coded by the nucleotide sequences according to the invention as well as the alleles and the derivatives of the latter which have the same function.

Also a subject of the present invention is the peptides constituted by or composed of a peptide sequence coded by all or part of the sequence 108 to 364 of SEQ ID No. 11.

In a general fashion, the present invention encompasses the peptides constituted by or composed of a peptide sequence coded by the nucleotide sequences according to the invention as well as fragments of these peptides. It also encompasses the peptides which differ from the latter by one or more amino acids and which have the same function. These peptides can correspond to modifications such as those known with muteins or to allelic variations. In fact it has been shown in particular that certain genetic segments coding for the variable regions of chains of T receptors in man were subjected to a phenomenon of genetic polymorphism called allelic variation (25). The present invention encompasses the peptides resulting from this phenomenon.

The nucleotide sequences according to the invention have been obtained according to the following stages:
  isolation of the RNA's of peripheral lymphocytes of an individual;
  obtaining the complementary DNA using reverse transcriptase and a primer A which is specific to the Cα region (SEQ ID No. 21);
  genetic amplification (by Anchored Polymerase Chain Reaction or A-PCR) using a DNA polymerase, a poly C primer (SEQ ID No. 22) and a primer B which is specific to the Cα region (SEQ ID No. 23);
  a new amplification by A-PCR using DNA polymerase and a primer C which is specific to the Cα region (SEQ ID No. 24);
  insertion in a plasmid vector;
  transformation of a bacterial host with the recombinant vector;
  screening of recombinant bacterial colonies with a labelled oligonucleotide D which is specific to Cα (SEQ ID No. 25);
  extraction of plasmids from positive colonies;
  and sequencing of DNA fragments containing the Cα region.

The present invention can be reproduced, in particular, by bispecific genetic amplification (polymerase chain reaction or PCR) by starting with the peripheral lymphocytes which express the mRNA including the variable or junctional segments corresponding to sequences ID No. 1 to 13 and 15 to 20 of the invention or alternatively by applying this PCR technique to genomic DNA of any somatic cell of an individual taken at random. The invention can also be reproduced by preparing the above genetic sequences by the chemical synthesis of oligonucleotides.

The peptides according to the invention can be obtained by standard peptide synthesis. They can also be obtained by the application of known genetic engineering techniques including the insertion of a DNA sequence coding for a peptide according to the invention into an expression vector such as a plasmid and the transformation of cells with this expression vector.

Therefore a subject of the present invention is also plasmids and expression vectors containing a DNA sequence coding for a peptide according to the invention as well as the hosts transformed with this vector.

Also a subject of the present invention is antibodies, and, in particular, monoclonal antibodies directed, against an antigenic determinant belonging to or composed of a peptide according to the invention.

The monoclonal antibodies may be obtained by any of the techniques which allow the production of antibody molecules from cell line culture. These techniques include different techniques using hybridomas.

The antibody production may be obtained in animals by the immunization of the animals by injection with the peptides or fragments according to the invention, whether they be natural, recombinant or synthetic, optionally after coupling to an immunogen such as tetanic anatoxin, or also by injection of human T lymphocytes expressing the corresponding sequences at their surface, including recombinant cells transfected with the corresponding coding sequences.

Also a subject of the present invention is hybridomas producing monoclonal antibodies directed against the polypeptides according to the invention.

The present invention also encompasses the fragments and the derivatives of monoclonal antibodies according to the invention which are reactive with defined variable regions of T-cell receptors. These fragments are, in particular, the F(ab')$_2$ fragments which can be obtained by the enzymatic leavage of antibody molecules with pepsin, the Fab' fragments which can be obtained by reduction of the disulphide bridges of F(ab')$_2$ fragments and the Fab fragments which can be obtained by the enzymatic cleavage of antibody molecules with papain in the presence of a reducing agent. These fragments can also be obtained by genetic engineering.

The monoclonal antibody derivatives are for example antibodies or fragments of these antibodies to which labellers such as a radio-isotope are attached. The monoclonal antibody derivatives are also antibodies or fragments of these antibodies to which therapeutically active molecules are attached, in particular, cytotoxic compounds.

The products of the invention have several uses in the field of diagnostics and in the field of therapeutics.

1—Uses in the Field of Diagnostics

The oligonucleotides contained in the nucleotide sequences according to the invention can be used to constitute detection probes (generally at least 10. nucleotides) which are capable of hybridizing with a variable region of the α chain or primers for the amplification of DNA (generally containing at least 15 nucleotides and preferably at least 17 nucleotides) which are capable of being linked to a sequence to be amplified.

Thus the oligonucleotides are used in the diagnosis of immune disorders by detecting the presence of nucleic acid sequences which are homologues of a gene coding for the variable regions of chains of T-cell receptors in the mRNA of a sample from a patient. Different methods can be used to establish a connection between the expression of T-cell genes and an illness. These methods include:
  a—the production and analysis of cDNA expression libraries-obtained from T-cells connected with the illness to determine the frequency of dominant genes;

b—Southern blot analysis of samples of genomic DNA to determine whether genetic polymorphisms or rearrangements of the genes coding for the T-cell receptors exist;

c—the analysis of samples by obtaining cDNA, amplification by PCR and hybridization with labelled probes;

d—the hybridization in situ of T-cells without culture of T-cells beforehand.

The primers are used in PCR reactions in a method such as that defined in c above.

The monoclonal antibodies, the fragments or the derivatives of these antibodies according to the invention, in particular the anti Vα antibodies, can be used to study T-type immune responses, for example in the field of the autoimmune diseases of oncology of allergies, of transplants and of infectious diseases. In particular, the directory of different variable α segments of the T receptor can be studied, whether it be blood or tissue T-cells. In a general fashion the techniques used can be in vitro or in vivo methods.

With in vitro methods, the samples used can be samples of body fluids or tissue samples. The techniques used can include in particular flow cytofluorimetry to analyse blood T lymphocytes or labelling with immunoperoxidase on an anatomopathological section to study the lymphocytes infiltrating the tissues.

With in vivo methods, the antibodies, their fragments or their derivatives are administered by the usual routes, for example by intravenous route, and the immunospecific linkages are detected. This can be obtained for example in the case where an antibody is used which is labelled with a radio-isotope.

2—Uses in the Therapeutic Field

The oligonucleotides contained in the nucleotide sequences according to the invention can be used in therapeutics as anti sense oligonucleotides. In fact it is known that it is possible in vitro to inhibit the expression of a transcript gene in human lymphocytes by incubating these lymphocytes with an anti sense oligonucleotide specific to the gene in question (26). These anti sense oligonucleotides generally contain at least 10 and, preferably, at least 16 nucleotides. These anti sense oligonucleotides can be in particular the inverted and complemented sequences corresponding to 20 nucleotides upstream from the initiation site of the translation (ATG). The significance of the use in vitro of anti sense oligonucleotides specific to a Vα or Jα genetic segment is to abolish (or strongly diminish) the expression of a T receptor containing this Vα or Jα segment and thus to obtain a phenomenon of clonal deletion at the level of the specific reactivity of T lymphocytes. The anti sense oligonucleotides can not only be used in vitro on human T lymphocytes which are then reinjected, but also in vivo by local or systemic injection preferably after modification to increase the stability in vivo and the penetration into the T lymphocytes of these oligonucleotides.

The monoclonal antibodies according to the invention, in particular the anti Vα antibodies can be used to modulate the immune system. It is in this way that the antibodies can be administered to block the interaction of the effector T-cells with their specific antigen. Anti T receptor antibodies linked for example to a cytotoxic molecule or a radio-isotope can also be administered in a way so as to obtain a clonal deletion, thanks to the specific fixation on an α chain of a T-cell receptor. The monoclonal antibodies according to the invention can be used in therapeutics at low mitogenic concentrations so as to activate, in a specific fashion, certain sub-assemblies of T-cells or can be used at much higher concentrations to fix them to the receptors concerned and thus label these sub-assemblies with a view to their elimination by the reticulo-endothelial system. An important criterion in the treatment of an illness is the ability to modulate the sub-assemblies of T-cells linked with an illness. The exact nature of this therapeutic modulation, namely blocking or suppressing a particular sub-assembly of T-cells or on the contrary stimulating and activating a particular sub-assembly, will depend on the illness in question and the specific sub-assembly of T-cells concerned.

This type of treatment has an advantage over current treatments using antibodies such as the treatment with anti CD3 antibodies in patients having had a kidney transplant and having a rejection problem, given that thanks to the invention there will be no modulation of the totality of the T-cell population but only of the sub-assembly of T-cells expressing the α sub-family specific to the T-cell receptors.

Moreover, as the response of T-cells is often oligoclonal, it is generally convenient to use "cocktails" of several antibodies in therapeutics.

In addition anti Vα antibodies can be used to select T lymphocytes in vitro, for example by passing through a column containing spheres carrying the antibody. This separation of certain T lymphocytes can be used with a view to culturing these lymphocytes before reinjection into the patient.

Moreover, all or part of the peptide sequences according to the invention can be used in therapeutics, that is to say the peptide sequences coded by the nucleotide sequences according to the invention or fragments of these sequences (generally containing at least 8 to 10 amino acids). These sequences or these fragments, administered to humans or animals, can act as a decoy, that is to say they fix themselves on the epitope carried by the harmful antigen and stop the reaction of normal T-cells with the antigen, preventing in this way the development of an illness which is aggressive towards the self determinants. They can also be used as immunogens in the manufacture of vaccines (optionally after conjugation with protein carriers).

The present invention will be described in greater detail hereafter by referring to the annexed figures in

BRIEF DESCRIPTION OF THE DRAWINGS

FIGS. 1A to E show in a line both a known V sequence and a partial sequence of an extension according to the invention for the respective sequences SEQ ID No. 6 to 10, marked IGRa 08 to IGRa 12. In these figures, the numbering of nucleotides starts at the ATG initiation codon (which is underlined). The dots indicate identical nucleotides. The sequences which are assumed to be the leader sequences have a line over them. Also shown in FIG. 1A is sequence AE11 (SEQ ID NO:63). In FIG. 1B, sequence AF110, consisting of nucleotides 78–330 of SEQ ID NO:7 is also shown. In FIG. 1C, sequence HAP35, consisting of nucleotides 152–400 of SEQ ID NO:8 is also shown. In FIG. 1D, sequence HAP12, consisting of nucleotides 69–290 of SEQ ID NO:9 is also shown. And in FIG. 1E, sequence AC9, consisting of nucleotides 271–383 of SEQ ID NO: 10 is also shown.

FIG. 2 shows in a line the new Jα sequences (SEQ ID No. 12, 13 and 15 to 20) marked IGRJa 01, 02 and 04 to 09. In these sequences the recombination signals of the germinal line are underlined. The amino acids corresponding to highly preserved codons are marked above the sequences. The codons corresponding to a substitution in one position of a preserved amino acid are underlined twice.

I—OBTAINING THE cDNA AND AMPLIFICATION BY PCR

Figure 3:
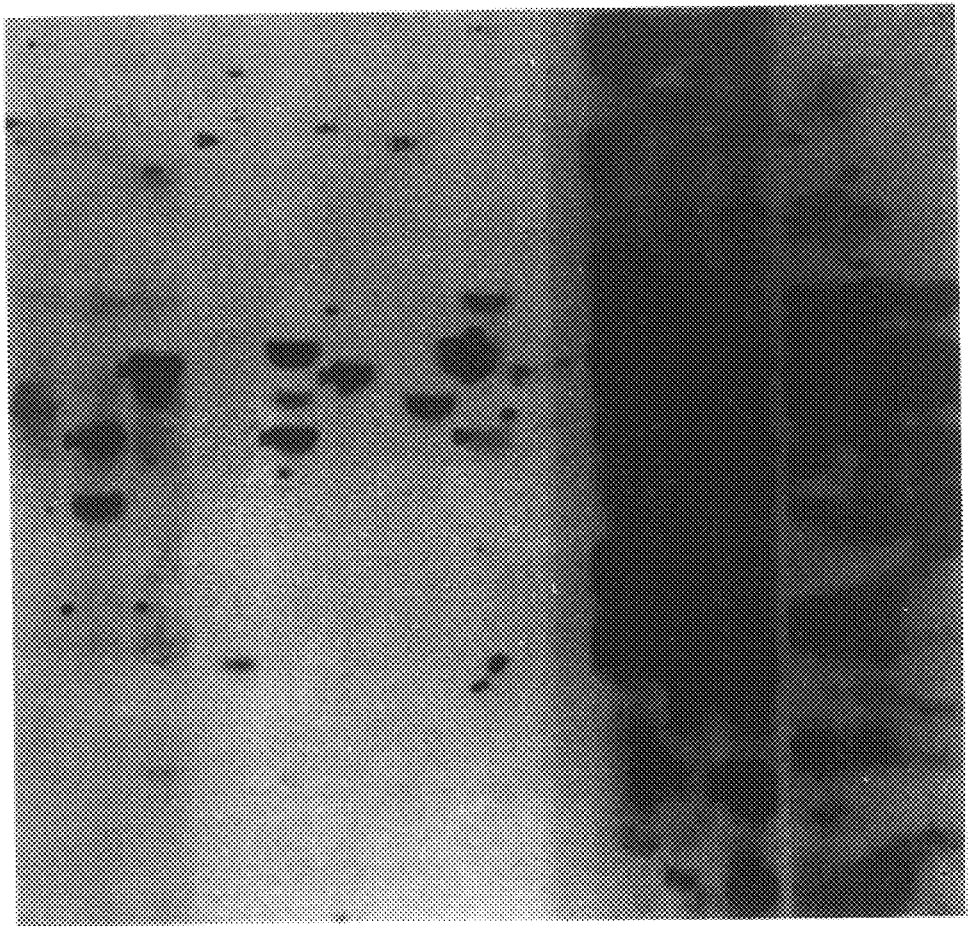
FIG. 3 shows the Southern blot analyses of the genomic DNA treated with a restriction enzyme using probes specific to sequences SEQ ID No. 1 to 5. The restriction enzymes used are EcoRI (column R), Hind III (column H) and Bam III (column B). On this figure the triangles mark the position of DNA fragments hybridizing in a specific fashion with Cα.

The peripheral lymphocytes of an individual are used as the DNA source. The total RNA was prepared according to the method using guanidinium isothiocyanate and caesium chloride (Chirgwin (10)) or according to a one-stage method by extraction with guanidinium isothiocyanate, phenol and chloroform (Chomcyznski (11)).

The first cDNA strand was synthesized in a final volume of 50 microlitres at a temperature of 42° C. for 1 hour using 5 micrograms of total RNA, reverse transcriptase and a primer A which is specific to the Cα region constituted by the sequence 5'-GTTGCTCCAGGCCACAGCACTG (SEQ ID No. 21). This material was then purified by extraction with phenol/chloroform and precipitation with ammonium acetate. After selecting a $^{0.45}/_1$ kb fraction on agarose gel, the addition of a dG end is carried out on the RNA/cDNA hetero complex in a $CoCl_2$ addition buffer with 14 units of terminal deoxynucleotidyl transferase (TdT) for 30 minutes at 37° C. The reaction was stopped by maintenance at 70° C. for 10 minutes. 1N NaOH (⅓ volume) was added and the sample was incubated at 50° C. for 1 hour to hydrolyze the RNA, then neutralized with Tris HCl 2M pH 8 and 1N HCl. After extraction with a phenol/chloroform mixture the first cDNA strand at end G was precipitated with ethanol and subjected to an amplification using the PCR technique (Polymerase Chain Reaction described by Saiki et al. (12)) in a final volume of 100 microlitres containing 50 mM of KCl, 10 mM of Tris-Cl pH 8.3, 1.5 mM of $MgCl_2$, 0.1% (weight/volume) of gelatine, 200 micromoles of dNTP, 2.5 units of Taq polymerase and 100 picomoles of two primers. The two primers used are, on the one hand-a poly-C primer (5'-GCATGCGCGCGGCCGCGGAGG-14C) (SEQ ID No.22) described by Loh et al. (13) as well as a primer B specific to the C region (5'-GTCCATAGACCTCATGTCCAGCACAG) (SEQ ID No. 23).

25 amplification cycles are carried out followed by a final 15 minute elongation period at 72° C. Each cycle includes a denaturation stage at 92° C. for 1 minute, a hybridization stage at 55° C. for 2 minutes and an elongation period at 72° C. for 4 minutes. The amplified products are then precipitated with ethanol, resuspended in 30 mM of sodium acetate pH 5, 50 mM NaCl, 1 mM $ZnCl_2$, glycerol 5% by volume and ¹/₁₀ of this material is purified as a function of size on a 1% low melting point agarose gel.

A second amplification phase is then carried out directly on approximately 10% of the band containing the agarose following the same conditions as previously, except that the primer 5'-ATACACATCAGAATTCTTACTTTG (SEQ ID No. 24) is used as primer C which is specific to the Cα region. The reaction mixture is then precipitated with ethanol and resuspended in 60 μl of $H_2O$.

II—Cloning and Sequencinq of cDNA's

⅓ of the product of the second amplification is digested with Sac II, separated on 1% agarose gel and purified by absorption on glass beads. The material is inserted in the Bluescript SK$^+$ vector (Stratagene, La Jolla, U.S.A.) and the recombinants obtained are used to transform the XL1-blue strains of *E. Coli* (Stratagene). After sedimentation in the presence of X-gal and IPTG, a test is carried out on the white colonies using a "dot blot" technique and a third oligonucleotide specific to the Cα region (5'-GTCACTGGATTTAGAGTCT) (SEQ ID No. 25) labelled with $^{32}p$ is used as a probe. The plasmid DNA of positive colonies is extracted and sequencing takes place under the two strands by the process of termination of the dideoxy chain (Sanger et al. (14)) with Sequenase 2.0 (United States Biochemicals, Cleveland, U.S.A.) following the supplier's recommendations. With the exception of the Sequence SEQ ID No. 5, all the nucleotide sequences were determined on the two strands using at least two distinct clones of cDNA.

The sequences obtained were compared with published Vα and Jα sequences using the method developed by Lipman and Pearson (15). The presumed start codons were identified by searching for the presence of the Kozak consensustsequence for the initiation sites of translations in the eukaryotic cells (Kozak (16)). The presence of hydrophobic leader sequences of the N-terminal side was detected by analysis of the hydrophobicityaccording to the method described by Kyte (17).

III—Southern Blot Analysis

The DNA was extracted from the human erythroleucemic cell line K562 and digested with one of the following restriction enzymes: EcoR I, BamH I or Hind III. The DNA (15 micrograms) was subjected to electrophoresis on 0.7% agarose and transferred onto Nylon membranes as described by Triebel et al. (18). The hybridizations were carried out at 65° C. with 6×SSC, 0.5% of SDS, 5× Denhardt's and 100 micrograms of denatured salmon sperm DNA for 16 hours. The membranes were washed at 65° C. with 2×SSC, 0.2% of SDS.

As Vα specific probes, are used the probes obtained by amplification of V-J-C cDNA (>500 bp) containing Vα fragments corresponding to sequences SEQ ID No. 1 to 5 using as a primer the poly-C primer and the C primer. The probes were purified on 1% agarose gel. DNA probes labelled with 32p were prepared from fragments purified on agarose by the Feinberg method (19).

IV—Results

By using the A-PCR method, 308 cDNA which hybridize with the Cα clone were cloned, then sequenced. Among these, 172 cDNA correspond to the V-J-Cα variable regions only.

The Vα and Jα sequences of the invention are shown in the list of sequences under SEQ ID No. 1 to 11 and SEQ ID No. 12, 13 and 15 to 20 respectively. The sequences SEQ ID No. 2 to 5 correspond to the new sub-families (designated Vα 25, Vα 26, Vα 27 and Vα 29 respectively) while the sequences SEQ ID No. 1 and 6 to 11 correspond to extensions of known V segments.

1. Vα Sequences Corresponding to New Sub-families

The-Southern blot analyses-of germinal line DNA subjected to digestion by endonucleases, using V-J-Cα probes containing Vα fragments corresponding to sequences SEQ ID No. 2 to 5 were carried out in "low stringency" hybridization conditions to identify the number of Vα genetic segments belonging to each family and to characterize the DNA restriction fragments carrying these Vα genetic segments. The representative results are shown in FIG. 3.

These analyses show that the sub-family corresponding to the sequence SEQ ID No. 3 includes at least two genetic segments while the other sequences (SEQ. ID No. 2, No. 4 and No. 5) probably correspond to unique members.

The sizes of the germinal DNA restriction fragments are as follows:

SEQ ID No. 2: EcoR I 2.2 kb, Hind III 4.8 and 5.7 kb, BamH I 25 kb

SEQ ID No. 3: EcoR I 4.6 and 7.5 kb, Hind III 4.2 and 6.4 kb, BamH I 23 and 4.5 kb SEQ ID No. 4: EcoR I 7.6 kb, Hind III 18 kb, BamH I 9 and 0.9 kb SEQ ID No. 5: EcoR I 5.9 and 4.8 kb, Hind III 6.6 kb, BamH I 6.5 kb.

2. Sequences Corresponding to Extensions of Known V Sequences

SEQ ID No. 1 (IGR a 02) corresponds to an extension of the 5' side of the LINV sequence (171 bp) (mengle-Gaw (20)): This sequence defines the sub-family provisionaly designated Vα w24.

SEQ ID No. 6 (IGR a 08): this sequence corresponds to an extension of the 5' side of the Vα 1 AE11 clone sequence (Klein et al. (21)). The two straight line sequences are represented in FIG. 1A.

SEQ ID No. 7 (IGR a 09): This sequence corresponds to an extension coding for the NH2 terminal end of the Vα 2 AF110 sequence (Klein already quoted). The two straight line sequences are represented in FIG. 1B. The sequence ID No. 7 corresponds to a consensus sequence. The existence of a T instead of a C is observed in position 206.

SEQ ID No. 8 (IGR a 010): This sequence corresponds to an al extension of the 5' region of the Vα HAP35 clone (Yoshikai (22)). The two straight line sequences are represented in FIG. 1C. The sequence ID No. 8 corresponds to a consensus sequence. The existence of a G instead of an A in position 307 and the existence of a T instead of a C in position 360 have been observed.

SEQ ID No. 9 (IGR a 11): This sequence corresponds to an extension of the 3' side of the Vα 7 HAP12 sequence (Yoshikai already quoted). The straight line of the sequences is represented in FIG. 1D. The sequence ID No. 9 corresponds to a consensus sequence. The existence of a C instead of a T in position 86 has been observed.

SEQ ID No. 10 (IGR a 12): This sequence includes the complete coding region of a gene of the Vα 22 sub-family which had been previously identified by the partial sequence (113 bp) AC9 (Klein already quoted). The two straight line sequences are represented in FIG. 1E.

SEQ ID No. 11 (IGR a 13): This sequence corresponds in part to the HAVT 32 and HAVT 35 clones (belonging to the Vα 16 (8) sub-family and which have been described as pseudogenes. In fact, following the addition of a nucleotide in position 108, the SEQ ID No. 11 codes for an original variable region of a T lymphocyte receptor. Moreover, this sequence is equivalent to a sequence HSTCAYM SEQ ID No:64 (Klein et al. (21)) for the coding part. However, the sequence SEQ No. 11 is the only one which is complete and coding.

3. Jα Sequences

The set of new Jα sequences are represented in FIG. 2. Among the 8 Jα segments, the majority of them have a highly preserved amino acid sequence FGXGT (SEQ ID No:65) of Jα segments as described by Yoshikai already quoted. However, for the IGRJa segment the threonine residue is replaced by an isoleucine residue.

In addition, instead of a phenylalanine residue a cysteine residue is found in IGRJa 02G.

The present invention also aims at providing specific oligonucleotides of different Vα sub-families, which can be used as primers for the amplification of DNA corresponding to these different Vα sub-families, with a view, for example, of a study of the expression of certain Vα sub-families in a patient and finally of a diagnosis of immune disorders, as indicated above.

The predominant expression of certain Vα sub-families has already been studied using an incomplete range of oligonucleotides. In this way Nitta et al. (29) have described the predominant expression of Vα 7 genes in the lymphocytes infiltrating the tumours. Moreover, Sottini et al. (30) have described the study of the directory of Vα's, in patients suffering from rheumatoid arthritis.

The present invention aims to provide a complete range of oligonucleotides allowing the study, of both known Vα sub-families and new Vα sub-families of the invention and which are completely specific to each sub-family. Thus the oligonucleotides have been chosen and synthesized to this end and to the requirements of modifications of one or two nucleotides which have been introduced relative to the natural sequences to reduce the cross-reactions between sub-families.

Thus a subject of the present invention is also oligonucleotides which can be used as primers for the amplification of DNA corresponding to the variable regions of α chains of T-cell receptors, chosen from the sequences SEQ ID No. 26 to 54.

Also a subject of the present invention is the use, as primers for the amplification of DNA corresponding to the variable regions of α chains of T-cell receptors, of oligonucleotides chosen from the sequences SEQ ID No. 26 to 54.

Also a subject of the present invention is a detection process of nucleotide sequences coding for the Vα segments of T receptors or of cDNA corresponding to transcription products of the latter, in a biological sample, characterized in that it includes:

a) the amplification of DNA with at least one pair of primers formed by one of the oligonucleotides chosen from the sequences SEQ ID No. 26 to 54 and one-oligonucleotide belonging to segment Cα, and b) the detection of amplified sequences with a Cα probe.

The oligonucleotide belonging to a Cα segment used for the amplification can be, in particular, chosen from the sequences SEQ ID No. 55 and 56.

To check the efficiency of the amplification, the operation is preferably carried out in the presence of a pair of control primers and the corresponding control sequence amplified using a corresponding control probe is detected.

This pair of control primers can correspond to two Cβ segments, for example the Cβ F and Cβ K primers corresponding to sequences SEQ ID No. 61 and 62. Then a Cβ detection probe is used (corresponding for example to the sequence SEQ ID No. 63). But this pair of primers can also be constituted by two primers belonging to β-actin, notably those corresponding to sequences SEQ ID No. 58 and 59. Then a detection probe corresponding to a sequence of β-actin, such as the sequence SEQ ID No. 60, is used.

Also a subject of the present invention is a diagnostic kit for the implementation of the process defined previously, which includes:

a) at least one oligonucleotide chosen from the sequences SEQ ID No. 26 to 54, b) a Cα primer,
c) a Cα probe.

In addition such a kit advantageously contains:
d) a pair of control primers,
e) a control probe.

This kit can contain in particular:
a) the group of 29 oligonucleotides corresponding to sequences SEQ ID No. 26 to 54,
b) a Cα primer chosen from the sequences corresponding to sequences SEQ ID No. 55 and 56,
c) a pair of control primers for β-actin having a sequence corresponding to sequences SEQ ID NO. 58 and 59 respectively,
d) a Cα probe corresponding to the sequence SEQ ID No. 57,
e) a control probe for β-actin corresponding to the sequence SEQ ID No. 60.

In the information given in the list of sequences for the sequences 26 to 60, the sequences SEQ ID No. 26 to 47 correspond to sequences belonging to clones of known Vα 1 to Vα 22 sub-families (available from the EMBL database) or to sequences which differ from them by one or two nucleotides.

The sequences SEQ ID No. 49, 50, 51, 52 and 54 correspond to sequences belonging to clones of new sub-families of the invention, corresponding to sub-families provisionally designated Vα w24, Vα w25, Vα w26, Vα w27 and Vα w29 (w indicating that the designation is pending definitive designation).

The sequences SEQ ID No. 48 and 53 correspond to sequences belonging to clones IGRa01 and IGRa06 respectively of known sub-families but having not yet received definitive designation (Vα w23 and Vα w28 respectively) one member element of which has already been described (Hinkkanen A. et al. (31) and Bernard O. et al. (32) respectively). The complete sequence of IGRaO6 has not yet been published.

The sequences SEQ ID No. 55 and 56 are two examples of oligonucleotides which can be used as Cα primers for amplification.

The sequence SEQ ID No. 57 is the sequence of a C probe which can be used for the detection of amplified DNAS.

The sequences SEQ ID No. 58, 59 and 60 are respectively the sequences of a pair of oligonucleotides belonging to the sequence of β-actin which can be used to check the amplification and the sequence of a probe for detecting the corresponding amplified DNAS.

In the list of sequences the position indicated is the position of the 5' end counting from the predicted initiation site of the ATG translation. In the case where the sequences are incomplete (unknown 5' region), the position (marked with an asterisk) is given relative to the first nucleotide of the sequence. The underlined nucleotides correspond to mismatches introduced relative to the natural sequence.

The oligonucleotides were sythesized with an Applied Biosystems 381 A automated DNA synthesizer using the β-cyano-ethylphosphoramidite method (Sinha N. et al. (33)) and following-the protocol recommended by the manufacturer. The oligonucleotides were detritylated in the apparatus, cleaved from the support and deprotected with ammonia (at 60° C. for 5 hours). The crude products were purified by reverse phase high pressure chromatography on a µ-bondapak C18 column using an acetonitrile gradient (9 to 15%) in a 0.01M triethylammonium acetate buffer at pH 5.5.

The amplification carried out using the primers according to the invention can be, in particular, the technique of amplification by PCR (Polymerase Chain Reaction) as described by Saiki et al. (12) and in Patents U.S. Pat. Nos. 4,683,195, 4,683,202, 4,889,818.

For the PCR, a double strand DNA can be used which is denatured or a cDNA obtained from RNA using reverse transcriptase as mentioned above.

The polymerization agent is a DNA polymerase, in particular, Taq polymerase.

Generally the amplification cycle is repeated 25 to 40 times.

The probes which are used for detecting the amplified sequences can be obtained by labelling the oligonucleotides with a radio-active isotope, which leads to detection by autoradiography, or by conjugation with an enzyme such as peroxidase (ECL Amersham system), alkaline phosphatase or β-galactosidase (Tropix Ozyme system), which leads to detection by chemiluminescence.

The following example illustrates the implementation of the detection process according to the invention.

The peripheral lymphocytes of a healthy individual were prepared by density gradient centrifugation. The total DNA was extracted according to a one-stage method by extraction with guanidium isothiocyanate, phenol and chloroform (Chomczynski, 11). The complementary DNA was synthesized in a final volume of 20 µl at 42° C. for one hour using 1 to 5 µg of total RNA, the reverse transcriptase and the Cα B primer (1.25 µM).

The material obtained was then heated at 95° C. for 3 minutes before being subjected to an amplification according to the PCR technique using in parallel each of the specific Vα primers corresponding to sequences SEQ ID No. 26 to 54 and the Cα B primer specific to the Cα region (SEQ ID No. 56). This amplification was carried out in a final volume of 10 µl per tube containing 50 mM of KCl, 10 mM of tris-HCl pH 8.3, 1.5 mM of $MgCl_2$, 0.1% (weight/volume) of gelatine, 200 µM of dNTP, 0.25 units of Taq polymerase and 0.25 µM of each primer. A control amplification was carried out in each tube from 25 mN of a DNA fragment of β-actin of 877 base pairs prepared by PCR and Act 1 and Act 2 primers (SEQ ID No. 58 and 59) specific to actin. 30 amplification cycles were carried out followed by a final elongation stage of 5 minutes at 72° C. Each cycle included a denaturation stage at 94° C. for one minute, a hybridization stage at 65° C. for one minute and an elongation period at 72° C. for one minute.

The products obtained were separated by electrophoresis on 2% agarose gel, transferred onto nylon membranes in an alkaline buffer and hybridized simultaneously with the Cα C oligonucleotide probes (SEQ ID No. 57) and Act 3 (SEQ ID No. 60) labelled with $^{32}p$ by the polynucleotidyl T4 kinase enzyme. The hybridization was carried out at 42° C. for 16 hours in a buffer containing 6×SSC, 0.5% SDS, 5x Denhardt's, 0.05% $NaH_2PO_4$ and 100 µg/ml of denatured salmon sperm DNA. The membranes were then washed with SSC 6x, 20 mM $NaH_2PO_4$, twice at ambient temperature for 5 minutes and once at 50° C. for 30 minutes then autoradiographed.

Figure 4:
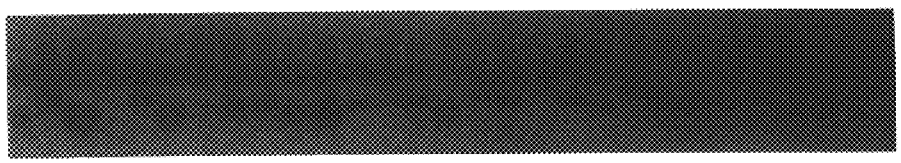
FIG. 4 represents the detection by autoradiography of amplified transcripts of TCR chains expressed by the peripheral lymphocytes of a healthy individual and of a co-amplified β-actin control.

The results obtained are shown in FIG. 4.

The actin control (band of 877 base pairs) allows the amplification to be verified in all wells. A specific signal appears below this band the size of which corresponds to the size of corresponding amplified fragments, each fragment having a length corresponding to the distance between the locus of the specific Vα oligonucleotide and the Cα primer.

With the individual tested, FIG. 4 shows the preferential expression of certain genetic segments defined relative to the others. For example, the Vα 27, 28 and 29 sub-families are less well represented than the Vα 2, 3 and 6 sub-families.

REFERENCES

1. Meuer, S. C., et al., J. Exp. Med. 1983. 157:705.
2. Moingeon, P., et al., Nature 1986a. 323:638.
3. Brenner, M. B., et al., Nature 1986. 322:145.
4. Bank, I., et al., Nature 1986. 322:179.
5. Davis, M. M., et al., Nature 1988. 334:395.
6. Crews, S., et al., Cell 1981. 25:59.
7. Concannon, P., et al., Proc. Natl. Acad. Sci. USA. 1986. 83:6598.
8. Kimura, N., et al., Eur. J. Immunol. 1987. 17:375.
9. Wilson, R. K., et al., Immunological Reviews 1988c. 101:149.
10. Chirgwin, J. M., et al. Biochemistry 1979. 18:5294.
11. Chomczynski, P., et al., Anal. Biochem. 1987. 162:156.
12. Saiki, R. K., et al., Science 1988. 239:487.
13. Loh, E. Y., et al., Science 1989. 243:217.
14. Sanger, F., et al., Proc. Natl. Acad. Sci. USA 1977. 74:5463.
15. Lipman, D. J., et al., Science 1985. 227:1435.
16. Kozak, M., Nucl. Acids Res. 1984. 12:857.
17. Kyte, J., et al., R. F., J. Mol. Biol. 1982. 157:105.
18. Triebel, F., et al., J. Immun. 1988. 140:300.
19. Feinberg, A. P., et al., Anal. Bichem. 1983. 132:6.
20. Mengle-Gaw, L., et al., The EMBO Journal, 1987. 6:2273.
21. Klein, M. H., et al., Proc. Natl. Acad. Sci. USA 1987. 84:6884.
22. Yoshikai, Y., et al., J. Exp. Med. 1986. 164:90.
23. Wandenback, A., et al., Nature, 341, 541.
24. Janeway, C., Nature, 341, 482.
25. Li, Y., J. Exp. Med., 171, 221.
26. Acha-Orbea, H., EMBO Journal, 1990,9, 12, 3815.
27. Kappler, J., Science 244, 811.
28. Choi, Y., PNAS, 86, 8941.
29. Nitta T. et al., Science 1990, 249, 672.
30. Sottini A. et al., Eur. J. Immunol., 1991, 21, 461.
31. Hinkkanen A. et al., Immunogenetics, 1989, 29, 131.
32. Bernard O. et al., Oncogene, 1988, 2, 195.
33. Sinha N. et al., Nucleic Acids Res. 1984, 12, 4539.

---

What is claimed is:

1. An isolated antibody that specifically binds a peptide coded by a nucleotide sequence coding for a variable region of α chain of an human T lymphocyte receptor, said nucleotide sequence having a nucleotide sequence chosen from any of:

Vα segments having any one of the sequences SEQ ID Nos. 1 to 11 or

Jα segments having one of the sequence SEQ ID Nos. 13 or 15 to 19.

2. An antibody of claim 1 wherein the nucleotide sequence is having any one of the nucleotide sequences of:

1 to 200 of SEQ ID No. 1

1 to 467 of SEQ ID No. 6

1 to 77 of SEQ ID No. 7

1 to 151 of SEQ ID No. 8

291 to 386 of SEQ ID No. 9 or 1 to 260 of SEQ ID No. 10.

3. Antibody of claim 1 which is a monoclonal antibody.

4. A Fab, Fab' or (Fab')$_2$ fragment of a monoclonal antibody of claim 3.

5. A monoclonal antibody of claim 3 to which a detectable marker is attached.

6. A hybridoma producing an antibody of claim 1.

* * * * *